(12) United States Patent
Knodel

(10) Patent No.: US 8,844,788 B2
(45) Date of Patent: *Sep. 30, 2014

(54) TRUE MULTI-FIRE LINEAR CUTTER

(71) Applicant: Cardica, Inc., Redwood City, CA (US)

(72) Inventor: Bryan D. Knodel, Flagstaff, AZ (US)

(73) Assignee: Cardica, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/757,196

(22) Filed: Feb. 1, 2013

(65) Prior Publication Data

US 2013/0140343 A1  Jun. 6, 2013

Related U.S. Application Data

(63) Continuation of application No. 12/565,534, filed on Sep. 23, 2009, now Pat. No. 8,365,971.

(51) Int. Cl.
*A61B 17/068* (2006.01)
*A61B 17/072* (2006.01)
*A61B 19/00* (2006.01)

(52) U.S. Cl.
CPC ......... *A61B 17/068* (2013.01); *A61B 17/07207* (2013.01); *A61B 2017/07271* (2013.01); *A61B 2017/07278* (2013.01); *A61B 2017/07285* (2013.01); *A61B 2019/444* (2013.01)
USPC .................. 227/175.1; 227/176.1; 227/180.1

(58) Field of Classification Search
CPC ........... A61B 17/068; A61B 17/07207; A61B 2017/07278; A61B 17/072; A61B 2019/307
USPC ................................ 227/175.1, 176.1, 180.1
See application file for complete search history.

(56) References Cited

U.S. PATENT DOCUMENTS 3,581,551 A   6/1971   Wilkinson
3,650,453 A   3/1972   Smith, Jr.

(Continued)

FOREIGN PATENT DOCUMENTS

EP   1238634   9/2002
EP   1464287   10/2004

(Continued)

OTHER PUBLICATIONS

Gong, Shao Wei, "Perfectly flexible mechanism and integrated mechanism system design", Mechanism and Machine Theory, Jun. 17, 2004.

(Continued)

*Primary Examiner* — Michelle Lopez
(74) *Attorney, Agent, or Firm* — Cardica, Inc.

(57) ABSTRACT

One exemplary surgical apparatus may include an anvil assembly to which a staple holder assembly detachably connected; feeder belts positioned at least partially within the staple holder assembly; staples separably attached to each feeder belt; a wedge assembly slidable within and along the staple holder assembly, the wedge assembly including an engagement feature; and a deployment handle, where, upon closure of the anvil assembly and staple holder assembly relative to one another, the deployment handle engages the engagement feature; where the deployment handle is movable along the anvil assembly to drive the wedge assembly relative to the staple holder assembly, feeder belts and staples in order to deform at least one staple to a closed state and separate at least one closed staple from the corresponding feeder belt. One exemplary surgical method may include providing a surgical stapler having an anvil and a staple holder separably connected to the anvil, where the staple holder holds feeder belts and staples separably connected to each feeder belt; deploying, at least twice, a plurality of staples from the staple holder; and then removing the staple holder from the anvil.

16 Claims, 18 Drawing Sheets

(56) References Cited

U.S. PATENT DOCUMENTS

| | | |
|---|---|---|
| 3,899,914 A | 8/1975 | Akiyama |
| 4,086,926 A | 5/1978 | Green et al. |
| 4,228,895 A | 10/1980 | Larkin |
| 4,417,535 A | 11/1983 | Hannemann |
| 4,475,679 A | 10/1984 | Fleury, Jr. |
| 4,520,817 A | 6/1985 | Green |
| 4,573,368 A | 3/1986 | Kobayashi |
| 4,633,861 A | 1/1987 | Chow et al. |
| 4,762,260 A | 8/1988 | Richards et al. |
| 4,969,591 A | 11/1990 | Richards et al. |
| 5,083,695 A | 1/1992 | Foslien et al. |
| 5,156,315 A | 10/1992 | Green et al. |
| 5,192,288 A | 3/1993 | Thompson et al. |
| 5,395,034 A | 3/1995 | Allen et al. |
| 5,476,206 A | 12/1995 | Green et al. |
| 5,571,116 A | 11/1996 | Bolanos et al. |
| 5,655,698 A | 8/1997 | Yoon |
| 5,662,260 A | 9/1997 | Yoon |
| 5,692,668 A | 12/1997 | Schulze et al. |
| 5,810,855 A | 9/1998 | Rayburn et al. |
| 5,816,471 A | 10/1998 | Plyley et al. |
| 5,855,311 A | 1/1999 | Hamblin et al. |
| 5,894,979 A | 4/1999 | Powell |
| 5,918,791 A | 7/1999 | Sorrentino et al. |
| 5,964,774 A | 10/1999 | McKean et al. |
| 6,306,149 B1 | 10/2001 | Meade |
| 6,602,252 B2 | 8/2003 | Mollenauer |
| 6,716,232 B1 | 4/2004 | Vidal et al. |
| 6,817,508 B1 | 11/2004 | Racenet et al. |
| 6,843,403 B2 | 1/2005 | Whitman |
| 7,025,747 B2 | 4/2006 | Smith |
| 7,055,730 B2 | 6/2006 | Ehrenfels et al. |
| 7,097,089 B2 | 8/2006 | Marczyk |
| 7,140,527 B2 | 11/2006 | Ehrenfels et al. |
| 7,168,604 B2 | 1/2007 | Milliman et al. |
| 7,172,104 B2 | 2/2007 | Scirica et al. |
| 7,179,267 B2 | 2/2007 | Nolan et al. |
| 7,207,471 B2 | 4/2007 | Heinrich et al. |
| 7,213,736 B2 | 5/2007 | Wales et al. |
| 7,225,963 B2 | 6/2007 | Scirica |
| 7,225,964 B2 | 6/2007 | Mastri et al. |
| 7,234,624 B2 | 6/2007 | Gresham et al. |
| 7,238,195 B2 | 7/2007 | Viola |
| 8,365,971 B1 * | 2/2013 | Knodel ............ 227/175.1 |
| 2003/0120284 A1 | 6/2003 | Palacios et al. |
| 2003/0236551 A1 | 12/2003 | Peterson |
| 2005/0184121 A1 | 8/2005 | Heinrich |
| 2006/0011699 A1 | 1/2006 | Olson et al. |
| 2006/0041273 A1 | 2/2006 | Ortiz et al. |
| 2006/0151567 A1 | 7/2006 | Roy |
| 2007/0027472 A1 | 2/2007 | Hiles et al. |
| 2007/0034668 A1 | 2/2007 | Holsten et al. |
| 2007/0073341 A1 | 3/2007 | Smith et al. |
| 2007/0083234 A1 | 4/2007 | Shelton, IV et al. |
| 2007/0118163 A1 | 5/2007 | Boudreaux et al. |
| 2007/0125828 A1 | 6/2007 | Rethy et al. |
| 2007/0175950 A1 | 8/2007 | Shelton, IV et al. |
| 2008/0078807 A1 | 4/2008 | Hess et al. |

FOREIGN PATENT DOCUMENTS

| | | |
|---|---|---|
| EP | 1736104 | 12/2006 |
| JP | 2005160933 | 6/2005 |
| RU | 2080833 | 6/1997 |
| WO | 8101953 | 7/1981 |
| WO | 8501427 | 4/1985 |

OTHER PUBLICATIONS

Kolios, MD, et al. "Microlaparoscopy", Journal of Endourology, vol. 18, No. 9, Nov. 2004.

Lim, Jonas J.B. et al. "A review of mechanism used in laparoscopic surgical instruments", Mechanism and Machine Theory, 38, Feb. 25, 2003.

Lim, Jonas J.B. et al. "Application of Type Synthesis Theory to the Redesign of a Complex Surgical Instrument", Journal of Biomechanical Engineering, vol. 124, Jun. 2002.

Lim, Jyue Boon, "Type Synthesis of a Complex Surgical Device", University of Minnesota Thesis, Feb. 21, 2001.

Steichen, et al. "Mechanical Sutures in Surgery" British Journal of Surgery, vol. 60, No. 3, Mar. 1973, pp. 191-197.

* cited by examiner

US 8,844,788 B2

TRUE MULTI-FIRE LINEAR CUTTER

CROSS-REFERENCE TO RELATED APPLICATIONS

This patent application is a continuation application of U.S. patent application Ser. No. 12/565,534, filed on Sep. 23, 2009, issued as U.S. Pat. No. 8,365,971 on Feb. 5, 2013, the content of which is incorporated herein by reference in its entirety for all purposes.

FIELD OF THE INVENTION

The invention generally relates to surgical staples and stapling, and more specifically to multi-fire surgical staplers.

BACKGROUND

A linear cutter is a surgical tool that staples and cuts tissue, such as gastrointestinal tissue, to transect that tissue while leaving the cut ends hemostatic. A typical linear cutter holds a disposable single-use cartridge with several rows of staples, and includes an anvil opposed to the cartridge. The surgeon inserts the linear cutter through an opening in the body, orients the end of the linear cutter around the tissue to be transected, and compresses the anvil and cartridge together to clamp that tissue. Then, a row or rows of staples are deployed on either side of the transection line, and a blade is advanced along the transection line to divide the tissue.

During actuation of a linear cutter, the cartridge fires all of the staples that it holds. In order to deploy more staples, the linear cutter must be moved away from the surgical site and removed from the patient, after which the old cartridge is exchanged for a new cartridge. The linear cutter is then reinserted into the patient. The process of removing the endocutter from the patient after each use, replacing the cartridge, and then finding the surgical site again is tedious, inconvenient and time-consuming, particularly where a surgical procedure requires multiple uses of the linear cutter. Similar inconveniences may accompany the use of surgical staplers other than linear cutters.

BRIEF DESCRIPTION OF THE DRAWINGS

The use of the same reference symbols in different figures indicates similar or identical items.

DETAILED DESCRIPTION

Linear Cutter

Figure 1:
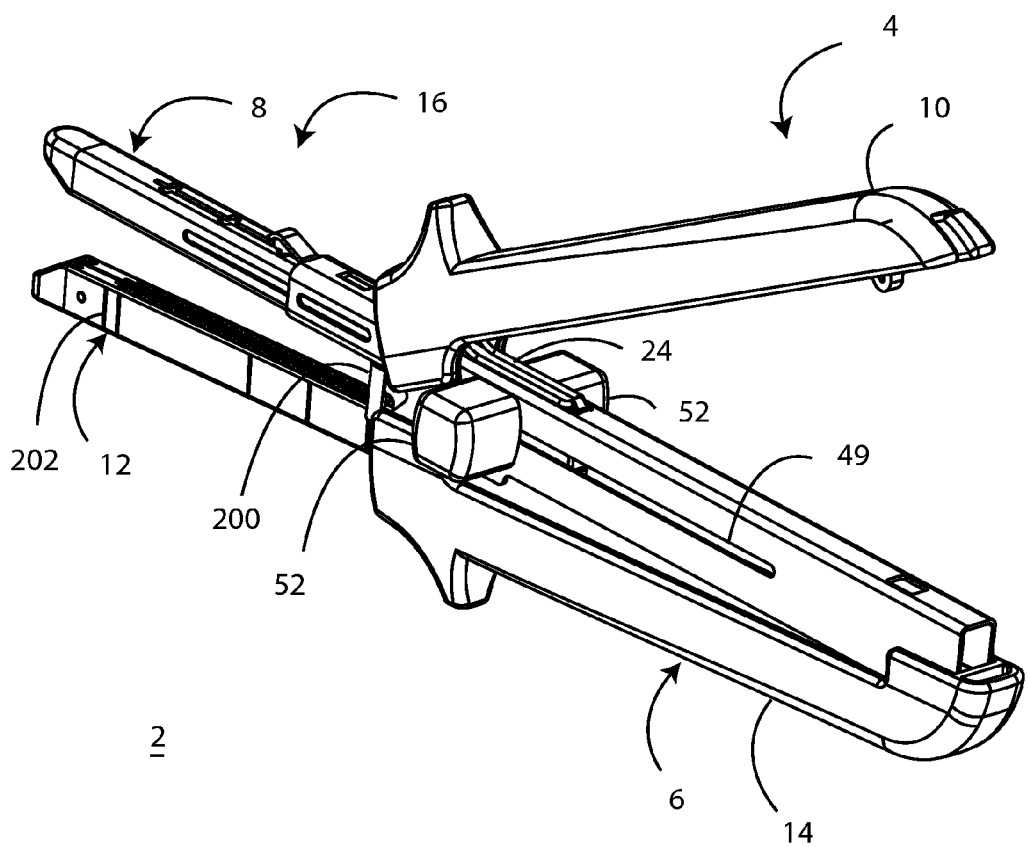
FIG. 1 is a perspective view of an exemplary linear cutter in a first, unclamped configuration.
Figure 2:
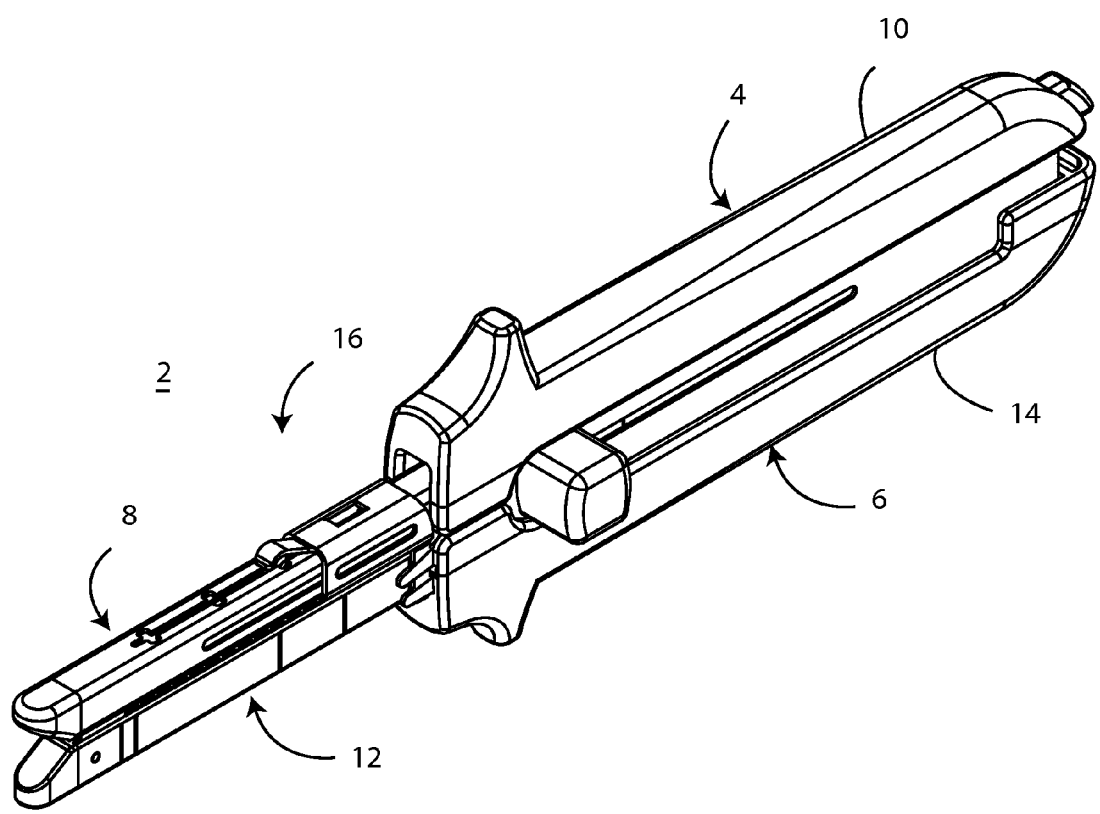
FIG. 2 is a perspective view of the exemplary linear cutter of FIG. 1 in a second, clamped configuration.

Referring to FIGS. 1-2, an linear cutter 2 includes an anvil assembly 4 detachably connected to a staple holder assembly 6. The linear cutter 2 is shown in a first, unclamped configuration in FIG. 1, and in a second, clamped configuration in FIG. 2. The anvil assembly 4 may include an anvil 8 connected to a first handle grip 10. The staple holder assembly 6 may include a staple holder 12 connected to a second handle grip 14. The portion of the linear cutter 2 extending distal to the handle grips 10, 14 may be referred to as the effector 16. The linear cutter 2 may be used in the course of conventional open surgery. Alternately, at least the effector 16 of the linear cutter 2 may be sized for insertion into the body of a patient through a laparoscopic incision, a trocar port, a hand-access device such as the LAP DISC® hand access device of Ethicon Endo-Surgery, Inc., or through any other access opening in the body of the patient. The staple holder assembly 6 is detachably connected to the anvil assembly 4, such that the two can be completely detached from one another.

The anvil 8 may be shaped in any suitable manner. As one example, at least the effector end 20 of the anvil 8 may be generally square or rectangular in cross-section, with an open volume 18 defined inside. In this document, the "effector end 20" of the anvil 8 is defined to mean the portion of the anvil 8 distal to the first handle grip 10. Proximal to that effector end 20, the anvil 8 may have a generally U-shaped cross-section, open toward the staple holder 12 to allow the anvil assembly 4 and staple holder assembly 6 to move closer together during clamping. However, the anvil 8 may be shaped in any other suitable manner. The surface of the effector end 20 of the anvil 8 may have one or more staple bending pockets defined therein, such as set forth in U.S. patent application Ser. No. 12/263,171, filed on Oct. 31, 2008, which is herein incorporated by reference in its entirety. The staple-bending pockets are oriented toward the staple holder 12.

The first handle grip 10 may be rotatably connected to the anvil 8 by a pin 22, where the first handle grip 10 is rotatable about the pin 22. The pin 22 may be located near the distal end of the first handle grip 10, and proximal to the effector end 20 of the anvil 8. The proximal end of the first handle grip 10 may be biased apart from the anvil 8 by a U-shaped wire 24. The wire 24 may be connected to the upper surface of the anvil 8 and extend into the distal end of the first handle grip 10, such that rotational motion of the first handle grip 10 downward toward the anvil 8 about the pin 22 compresses the wire 24. Such compression acts to urge the proximal end of the first handle grip 10 outward from the anvil 8. Alternately, the wire 24 may be replaced with a leaf spring, a plurality of wires, a wire shaped in a different manner, or any other suitable structure or mechanism.

Figure 4:
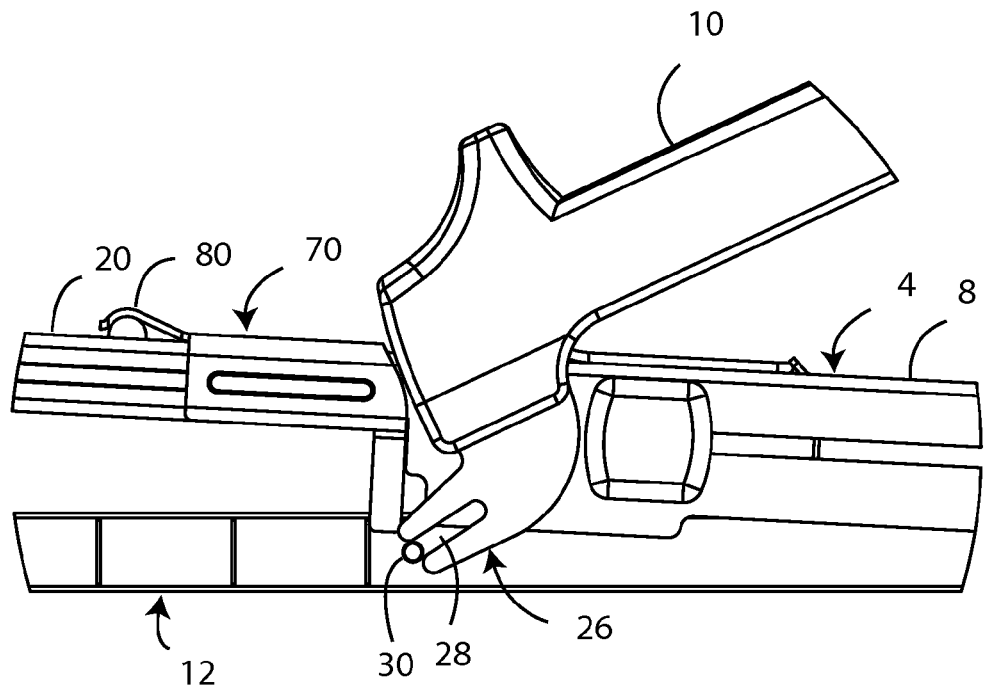
FIG. 4 is a side view of part of the exemplary linear cutter of FIG. 1 in the first, unclamped configuration.
Figure 5:
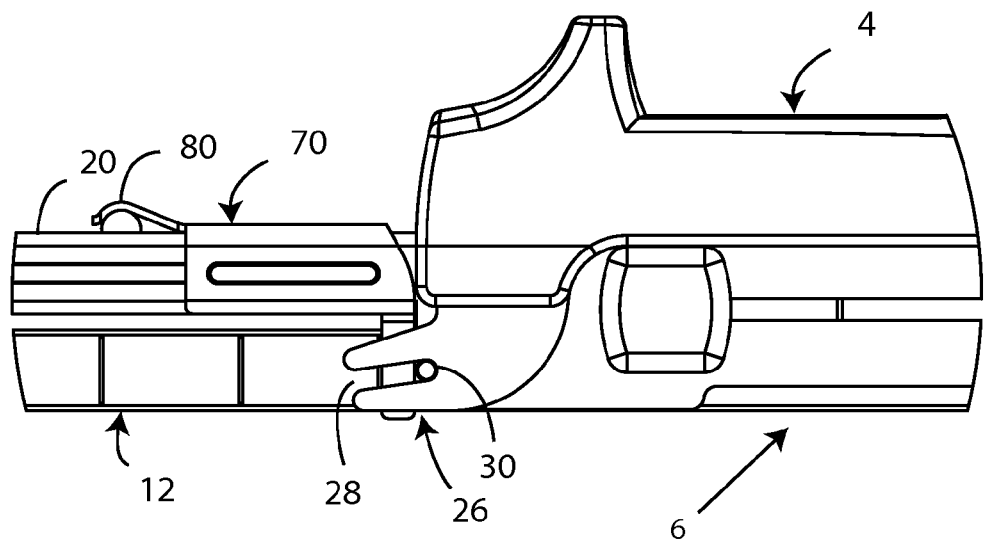
FIG. 5 is a side view of part of the exemplary linear cutter of FIG. 1 in the second, clamped configuration.
Figure 6:
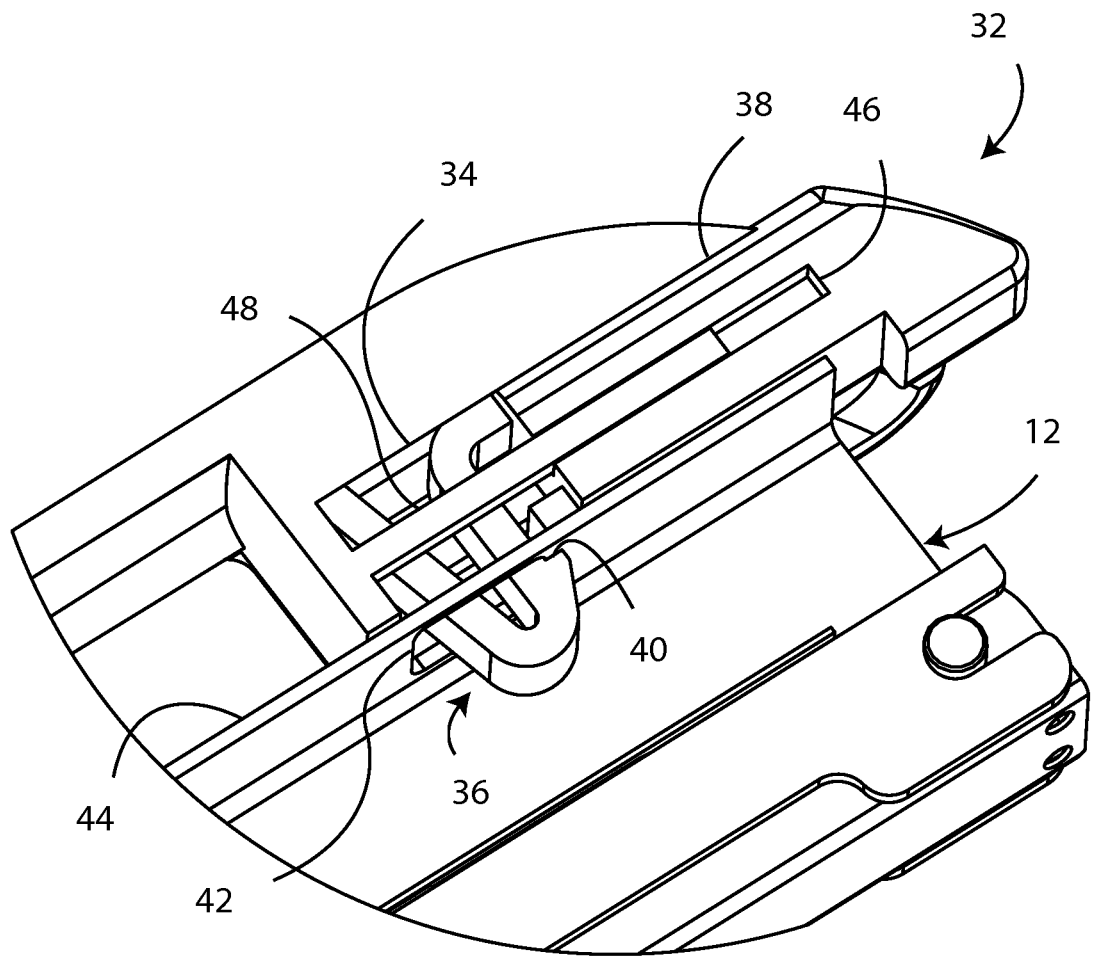
FIG. 6 is a perspective cutaway view of the proximal end of the exemplary linear cutter of FIG. 1 in the second, clamped configuration, showing an exemplary clamp latch.

Referring also to FIGS. 4-5, the distal end of the first handle grip 10 may include two forks 26. The forks 26 are positioned laterally outward from the anvil 8. Each fork 26 defines a slot 28 therein. The forks 26 may be positioned such that each slot 28 is oriented to engage a corresponding clamp pin 30 extending laterally from the staple holder 12. As the first handle grip 10 is compressed downward and rotates about the pin 22, each clamp pin 30 is grabbed by the corresponding fork 26, entering the slot 28 thereof. The slots 28 are shaped such that continuing rotary motion of the first handle grip 10 about the pin 22 causes the forks 26 to lift up the corresponding pins 22 and/or pull down the anvil 8, thereby clamping the anvil assembly 4 to the staple holder assembly 6 as seen in FIG. 5.

A clamp latch 32 may be positioned in a latch cavity 34 defined in the first handle grip 10. Advantageously, the clamp latch 32 may be located at the proximal end of the first handle grip 10. The clamp latch 32 may include a generally V-shaped living hinge 36, and a slider 38 connected to the proximal end of the living hinge 36. A ledge 40 may be defined on the living hinge 36. As the first handle grip 10 is compressed toward the staple holder assembly 6, the living hinge 36 enters a clamp slot 42 defined on an upper surface of the staple holder 12. The proximal portion of the living hinge 36 presses against the proximal end of the clamp slot 42, bending the living hinge 36 and pushing it distally. After the first handle grip 10 has been rotated sufficiently far about the pin 22, the ledge 40 enters the slot 42, and passes through the slot 42. After the ledge 40 passes through the slot 42, the living hinge 36 flexes back proximally, such that the ledge 40 may be seated against the inner part of the upper surface 44 of the staple holder 12, and such that the living hinge 36 may be pressed against the proximal end of the slot 42. The ledge 40 prevents the first handle grip 10 from rotating back upward about the pin 22, because it engages the upper surface 44 of the staple holder 12 proximal to the slot 40. In order to unclamp the anvil assembly 4 from the staple holder assembly 10, the slider 38 may be pushed distally. The slider 38 may slide within the latch cavity 34, and may be constrained to substantially longitudinal motion along the first handle grip 10 by a slider slot 46 defined therein that corresponds to a slider rail 48 defined in the latch cavity. As the slider 38 moves distally, the living hinge 36 is compressed distally, such that the ledge 40 moves distally out of engagement with the upper surface 44 of the staple holder 12 to a position underneath the slot 42. The ledge 40 is then free to move upward out of the slot 42, unlatching the anvil assembly 4 from the staple holder assembly 6.

Figure 7:
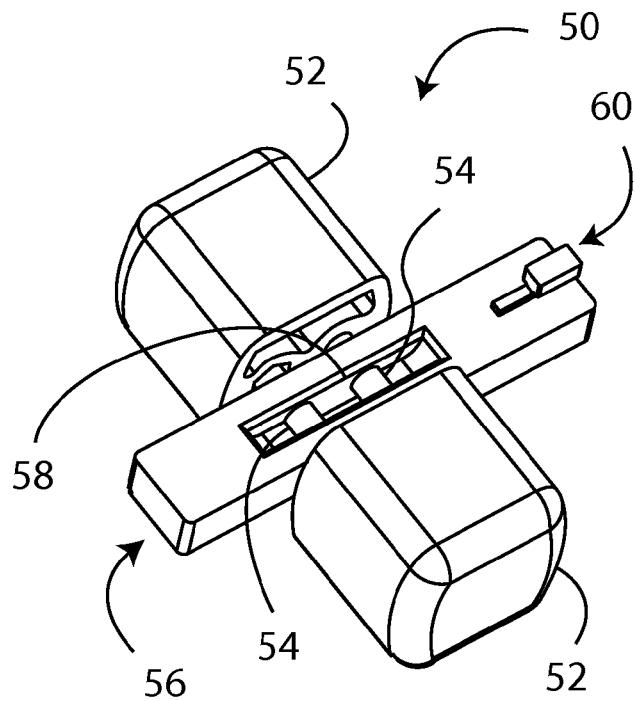
FIG. 7 is a perspective view of the underside of an exemplary deployment handle of the linear cutter of FIG. 1.
Figure 8:
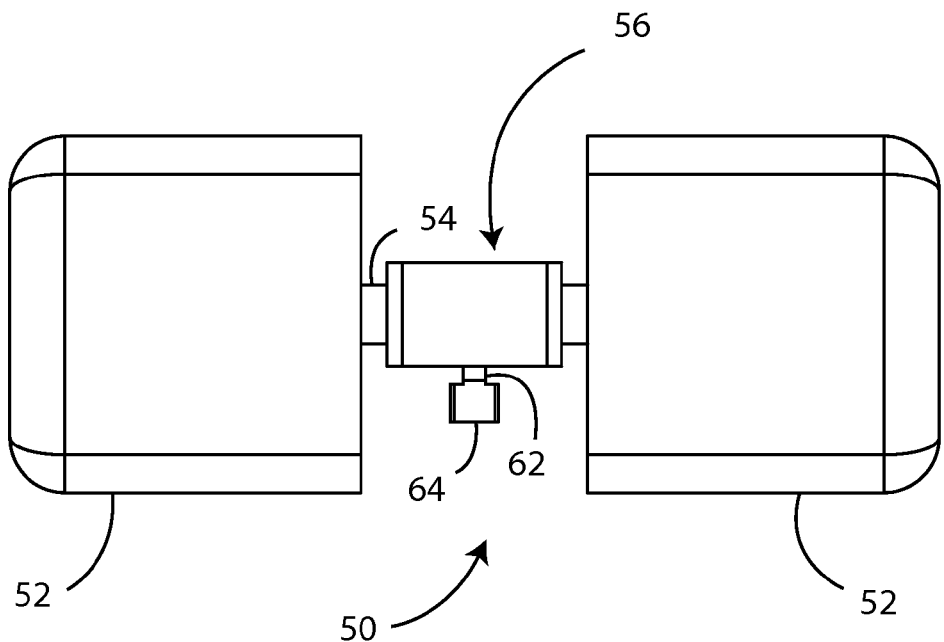
FIG. 8 is an end view of the deployment handle of FIG. 7.

The anvil 8 may be slotted along its sides. Referring also to FIG. 1, an actuation slot 49 extends generally longitudinally along each lateral side of the anvil 8. Referring also to FIGS. 7-8, the actuation slots 49 in the anvil 8 allow a portion of a deployment handle 50 to be received therethrough. The deployment handle 50 may be manually operable, and may include one or more grips 52 that may extend laterally to the anvil 8. At least one rod 54 may extend through both actuation slots 49 in the anvil 8. Advantageously, one grip 52 is located on each side of the anvil 8, and two rods 54 extend between the grips 52, through both actuation slots 49. The rods 54 may be longitudinally spaced from one another a fixed distance. A handle block 56 may be fixed to the grips 52 and/or the rods 54. The handle block 56 may have a cross-sectional shape and area slightly smaller than the cross-section of the interior of the anvil 8. In this way, the handle block 56 is slidable along the interior of the anvil, and acts to prevent cocking of the deployment handle 50 in the anvil 8. "Cocking" refers to undesired pitch, roll and/or yaw of the deployment handle 50 during travel that would impede its motion. The handle block 56 may include an aperture 58 defined at least partially therein, such that the rods 54 are visible from the underside of the handle block 56 and are accessible from that underside. Optionally, the rods 54 may be removed, and the aperture 58 may be sized longitudinally to have substantially the same length as the longitudinal spacing between the rods 54. A primer 60 may extend downward from the proximal end of the handle block 56, or from any other suitable location on the handle block 56. The primer 60 disengages a safety feature in the staple holder 12 and primes it for firing, as described in greater detail below. The primer 60 may have any suitable shape. As one example, the primer 60 may be substantially T-shaped as the handle block 56 is viewed on end, as seen in FIG. 8. The primer 60 may include a narrow downwardly-extending first member 62, and a wider laterally-extending second member 64 connected to the first member 62 and spaced apart from the lower surface of the handle block 56. Alternately, the primer 60 may be configured in any other suitable manner.

The deployment handle 50 may be configured in any other suitable manner that allows it to engage an engagement feature extending from the staple holder 12, as described in greater detail below. Alternately, rather than being actuated manually, the deployment handle 50 may include or be connectable to a source of stored energy for actuating the linear cutter 2. The source of stored energy may be mechanical (such as a spring), electrical (such as a battery or a connection to an electrical outlet), pneumatic (such as a cylinder of pressurized gas or a connection to a vacuum source) or any other suitable source of stored energy. The source of stored energy, its regulation, and its use in actuating the end effector 4 may be as described in the U.S. patent application Ser. No. 11/054, 265, filed on Feb. 9, 2005, which is herein incorporated by reference in its entirety.

Figure 9:
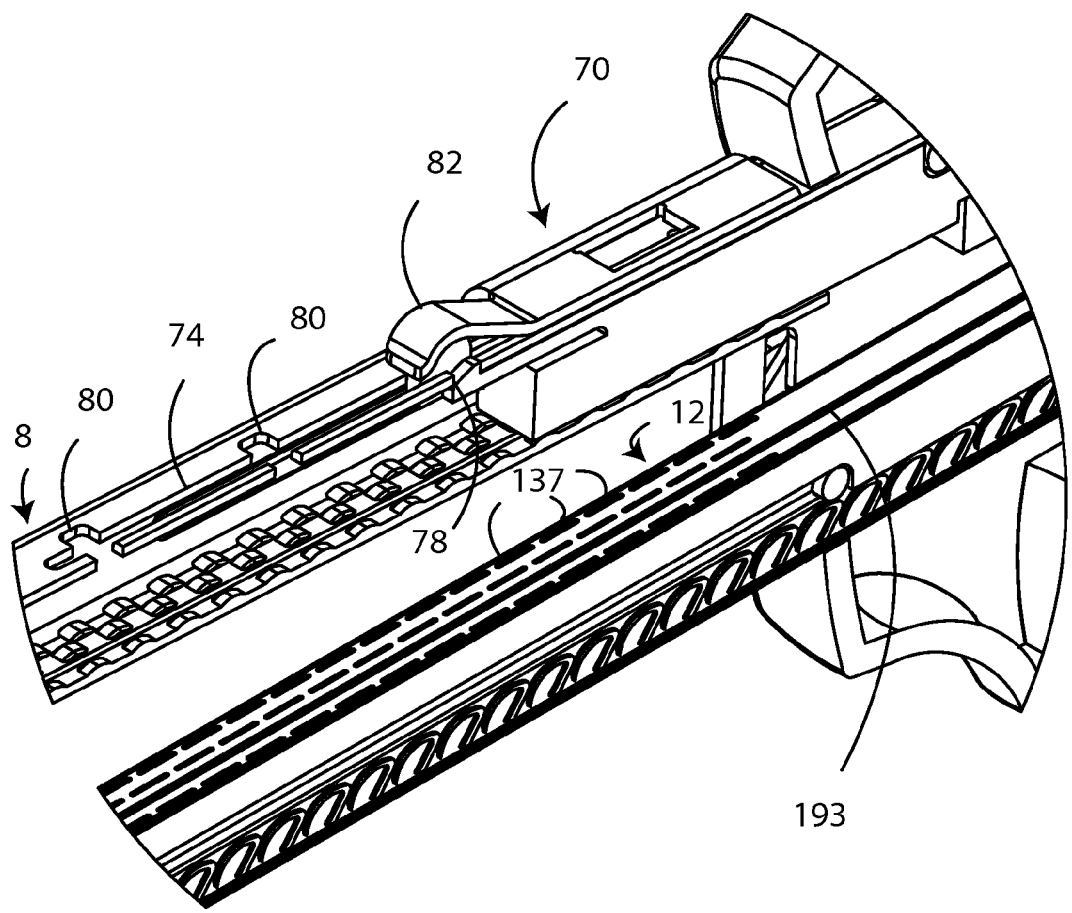
FIG. 9 is a perspective cross-section view from one side of the linear cutter of FIG. 1 of a portion of the anvil, and an exemplary adjustable tissue stop.
Figure 10:
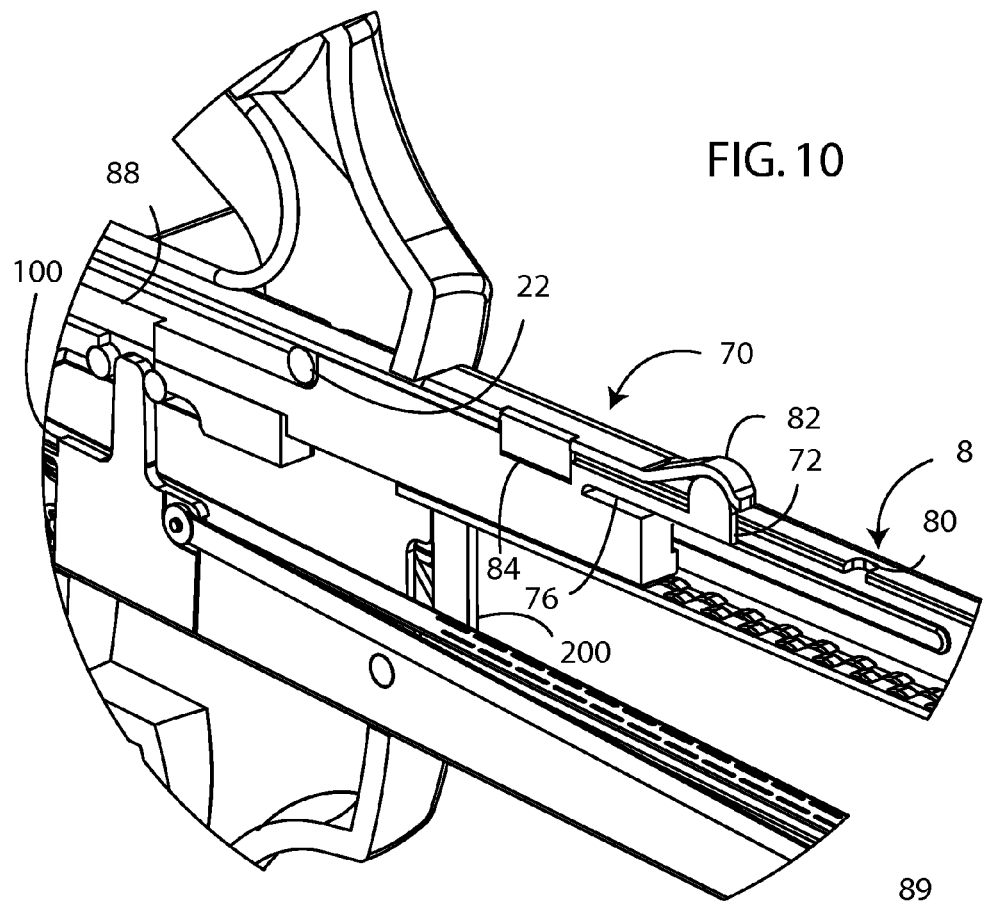
FIG. 10 is a perspective cross-section view from a different side of the linear cutter of FIG. 1 of a portion of the anvil, and an exemplary adjustable tissue stop.
Figure 11:
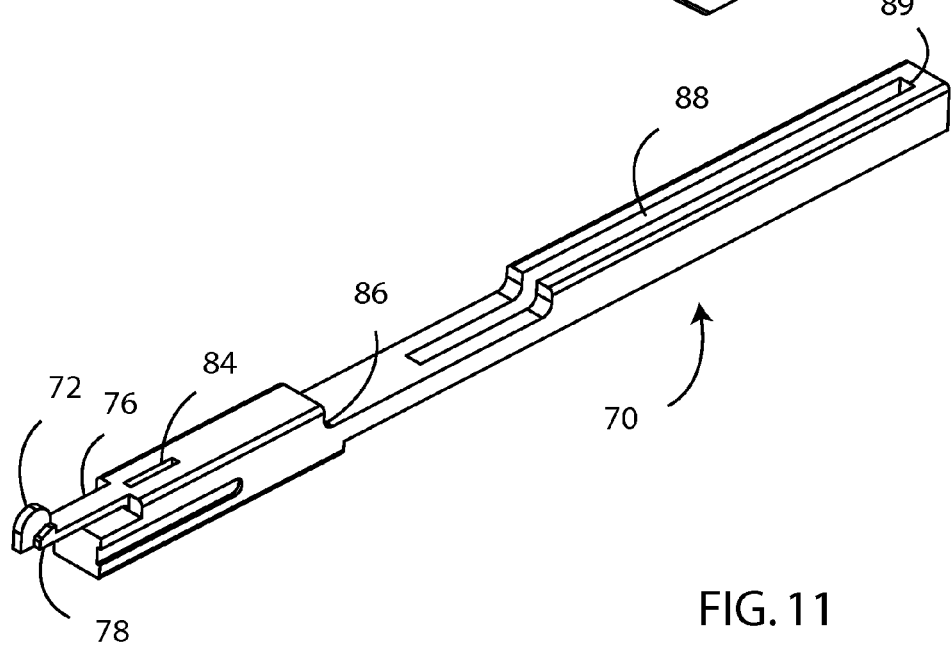
FIG. 11 is a perspective view of the exemplary tissue stop of FIGS. 9-10.

Referring to FIGS. 9-11, the linear cutter 2 may include an adjustable tissue stop 70. At or near the distal end of the adjustable tissue stop 70, a protrusion 72 may extend generally upward. The protrusion 72 may be curved along its upper surface, and may form a shape such as a semicircle. However, the protrusion 72 may have any other suitable shape. The protrusion 72 is configured to extend through a tissue stop slot 74 defined through the upper surface of the anvil 8. The tissue stop slot 74 may extend along part or all of the effector end 20 of the anvil 8, and may extend proximal to the effector end 20 if desired. The lateral thickness of the protrusion 72 is slightly less than the width of the tissue stop slot 74, to allow the protrusion 72 to easily slide along the tissue stop slot 74. The protrusion 72 may be located at the distal end of or on a different location on cantilever 76 that extends distally from a remainder of the adjustable tissue stop 70. Alternately, the cantilever 76 may be omitted and the protrusion 72 may extend from a different part of the adjustable tissue stop 70. The adjustable tissue stop 70 may include at least one latch 78 positioned adjacent to the protrusion 72. Advantageously, two latches 78 may be used, one on each side of the protrusion 72, such that the latches 78 are also positioned on the cantilever 76. Alternately, a different number of latches 78 may be used, and/or the latch or latches 78 may be located at a different position on the tissue stop 70. At least one latch 78 may be shaped such that its upper surface slopes upward toward the proximal direction, and such that the proximal end of the latch 78 is substantially vertical Alternately, at least one latch 78 may be shaped differently. At least part of at least one latch 78 is positioned lateral to a lateral edge of the tissue stop slot 74. One or more latching slots 80 may be defined through the upper surface of the anvil 8. For example, at least one latching slot 80 may be substantially rectangular, substantially transverse to the tissue stop slot 74, and may be substantially bisected by the tissue stop slot 74. Alternately, at least one latching slot 80 may be shaped or oriented differently. Each latching slot 74 is sized, shaped and oriented to allow at least one corresponding latch 78 to extend therein, such that the proximal end of the latch 78 abuts and is restrained against proximal motion by contact with the proximal edge of that latching slot 74. The adjustable tissue stop 70 may include a finger piece 82. The finger piece 82 may be positioned above the protrusion 72, and may be wider than the protrusion 72 in order to facilitate a user pressing down on the protrusion 72. Pressing down on the protrusion 72 bends the cantilever 76, moving each latch 78 downward out of engagement with the corresponding latching slot 80. The finger piece 82 may be pressure-fit or otherwise connected to a finger piece aperture 84 defined in a remainder of the adjustable tissue stop 70. Alternately, the finger piece 82 may be connected to a remainder of the adjustable tissue stop 70 in any other suitable manner, or may be fabricated integrally with a remainder of the adjustable tissue stop 70. A stop 86 may be defined in the adjustable tissue stop 70 at any suitable location thereon. The stop 86 may be a substantially vertical surface, or may be configured differently. The stop 86 may be configured to abut the pin 22 in the anvil assembly 4 when the adjustable tissue stop 70 is in its most-proximal position. In this way, the adjustable tissue stop 70 may be further constrained in its range of travel. A travel slot 88 may be defined in the lower surface of, or completely through, the adjustable tissue stop 70. The travel slot 88 may be oriented generally longitudinally, and may be generally rectangular in shape as viewed from above. However, the travel slot 88 may be shaped or oriented differently, if desired. At least the proximal end 89 of the travel slot 88 may be closed. Alternately, the adjustable tissue stop 70 may be slidable along the staple holder assembly 6 rather than, or in addition to, the anvil assembly 4. If so, the staple holder assembly 6 may be slotted in substantially the same manner as described above for the anvil assembly 4.

Referring to FIGS. 1-3 and 12, the staple holder 12 may be shaped in any suitable manner. As one example, at least the effector end 21 of the staple holder 12 may be generally square or rectangular in cross-section. In this document, the "effector end 21" of the staple holder 12 is defined to mean the portion of the staple holder 12 distal to the second handle grip 14. Proximal to that effector end 21, the staple holder 12 also may have a generally square or rectangular cross-section. However, the staple holder 12 may be shaped in any other suitable manner. An upper surface of the staple holder 12 includes a plurality of staple apertures 90 defined therethrough to allow staples to travel outward therethrough, as defined in greater detail below. At the distal end of the staple holder 12, two or more notches 92 may be defined in the upper surface of the effector end 21 of the staple holder 12. A nose 94 may be connected to the distal end of the effector end 21 of the staple holder 12, and may include features that fit into the corresponding notches 92. In this way, the nose 94 may resist forces that would attempt to rotate the staple holder 12 about its longitudinal axis, and thereby increase its torsional rigidity. The nose 94 optionally may be color coded to correspond to the size of staples that the staple holder 12 is configured to deploy. Colors associated with particular staple sizes are standard in the art.

Referring also to FIGS. 10 and 12-15, a wedge assembly 100 is slidable along the interior of the staple holder 12. The wedge assembly 100 includes an engagement feature 102 that extends upward relative to the staple holder 12. The engagement feature 102 may be shaped and sized in any suitable manner, and may be any suitable structure or mechanism. As one example, the engagement feature 102 may be a generally trapezoidal solid that tapers upwardly, which may be referred to as a "tail." The engagement feature 102 instead may be a rectangular solid, triangular solid, irregular solid, or other shape. As another example, the engagement feature 102 need not be solid, and instead may be slotted, may be composed of a plurality of frame or scaffold elements, or may be otherwise a non-solid component, as may be one or more other portions of the wedge assembly 100.

Referring also to FIGS. 7-8, the engagement feature 102 is configured to be engaged by the deployment handle 50. The rods 54 of the deployment handle 50 may be spaced apart from one another a distance substantially equal to the longitudinal dimension of the engagement feature 102, such that the engagement feature 102 is engaged between the rods 54 of the deployment handle 50 when the linear cutter 2 is in the closed position, as described in greater detail below. Alternately, the proximal and distal ends of the aperture 58 in the deployment handle 50 may be spaced apart from one another a distance substantially equal to the longitudinal dimension of the engagement feature 102, such that the aperture 58 itself engages the engagement feature 102. The engagement feature 102 may be shaped such that the closing of the linear cutter 2 results in smooth engagement of at least one proximal and/or distal surface of the engagement feature 102 during the entire action of closing the linear cutter 2. Alternately, the deployment handle 50 need not engage at least one proximal and/or distal surface of the engagement feature 102 during closing of the linear cutter 2. The engagement feature 102 may have a sufficient height, the deployment handle 50 may have a sufficient depth, and/or the anvil assembly 4 may be held within a close enough distance of the staple holder assembly 6 in the open, unclamped position such that at least part of the engagement feature 102 is held between the rods 54 of the deployment handle 50, or otherwise extends into the deployment handle 50, in both the open and closed configurations of the linear cutter 2. Alternately, the engagement feature 102 need not enter and/or otherwise be engaged by the deployment handle 50 until the anvil assembly 4 and/or staple holder assembly 6 is moved toward the other in order to close the linear cutter 2 to the closed position. Alternately, the deployment handle 50 may be configured to engage the engagement feature 102 in any other suitable manner when the linear cutter 2 is in the closed position. As one example, the deployment handle 50 may include an engagement feature that extends downward into the wedge 100 when the linear cutter 2 is in the closed position, and the wedge 100 may include two longitudinally-spaced bars, an aperture, or other receiver to receive that engagement feature from the deployment handle 50. As another example, the deployment handle 50 may actively engage the engagement feature 102, such as by the insertion of a pin, by clamping, or otherwise performing an action with one or more mechanisms to grasp and hold the engagement feature. Such active engagement may engage the wedge assembly 100 in such a manner such that the engagement feature 102 may be omitted. As another example, the deployment handle 50 may otherwise passively engage the engagement feature 102, such as by magnetic force. Such passive engagement may engage the wedge assembly 100 in such a manner such that the engagement feature 102 may be omitted.

Referring also to FIGS. 13-18, the wedge assembly 100 may include a cantilever 104 extending proximally, and a brick 106 extending from the cantilever 104. The brick 106 may be located at the proximal end of the cantilever 104, and may extend generally upward from the cantilever 104. Alternately, the brick 106 may be located and/or oriented differently on the cantilever 104. The cantilever 102 is biased upward, such that (before firing of the linear cutter 2) at least part of the brick 106 is positioned within a brick receiving slot 108 defined in the upper surface 44 of the staple holder 12. A longitudinal slot 110 may also be defined in the upper surface 44 of the staple holder 12, and the brick receiving slot 108 may be generally transverse to and wider than the longitudinal slot 110. The brick receiving slot 108 may be generally rectangular in shape, and the brick 106 may be shaped and sized substantially the same as the brick receiving slot 108. Alternately, the brick 106 and/or brick receiving slot 108 may be shaped and/or sized differently. The wedge assembly 100 may include one or more slits 112 defined therein to allow the wedge assembly 100 to slide along the longitudinal slot 110. That is, only the portion of the wedge assembly 100 at the same level as the upper surface 44 of the staple holder 12 need be as narrow as the longitudinal slot 110 in order to slide along the longitudinal slot 110; as a result, the slit or slits 112 in the wedge assembly 100 are deep enough to allow the wedge assembly 100 to slide along the longitudinal slot 110. Initially, the brick 106 resides at least partially in the brick receiving slot 108; this engagement prevents longitudinal motion of the wedge assembly 100 along the staple holder 12. As described in greater detail below, when the linear cutter 2 is moved to the closed position, the primer 60 of the deployment handle 50 engages and presses down upon the brick 106, moving the brick 106 out of engagement with the brick receiving slot 108 and freeing the wedge assembly 100 to slide along the staple holder 12. The brick 106 may be wider than the longitudinal slot 110, such that as the wedge assembly 100 slides along the staple holder 12, the brick 106 is positioned under the upper surface 44 of the staple holder 12, with at least one lateral side extending lateral to the longitudinal slot 110 in the upper surface 44 of the staple holder 12.

Figure 17:
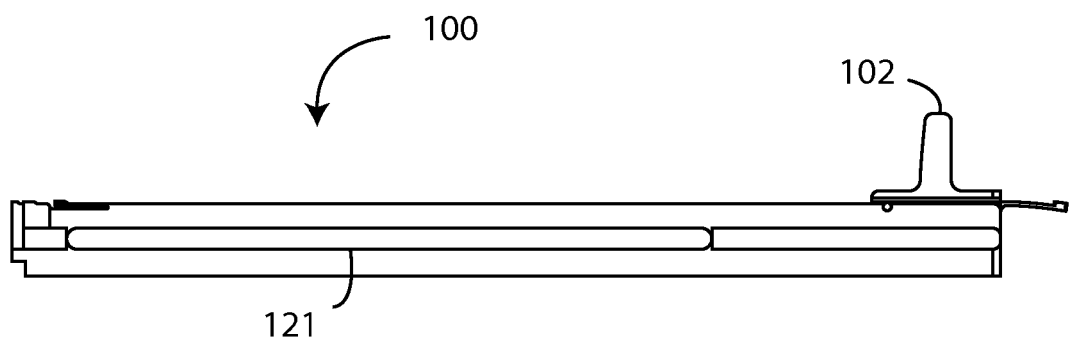
FIG. 17 is a side view of the exemplary wedge assembly of FIG. 16.
Figure 23:
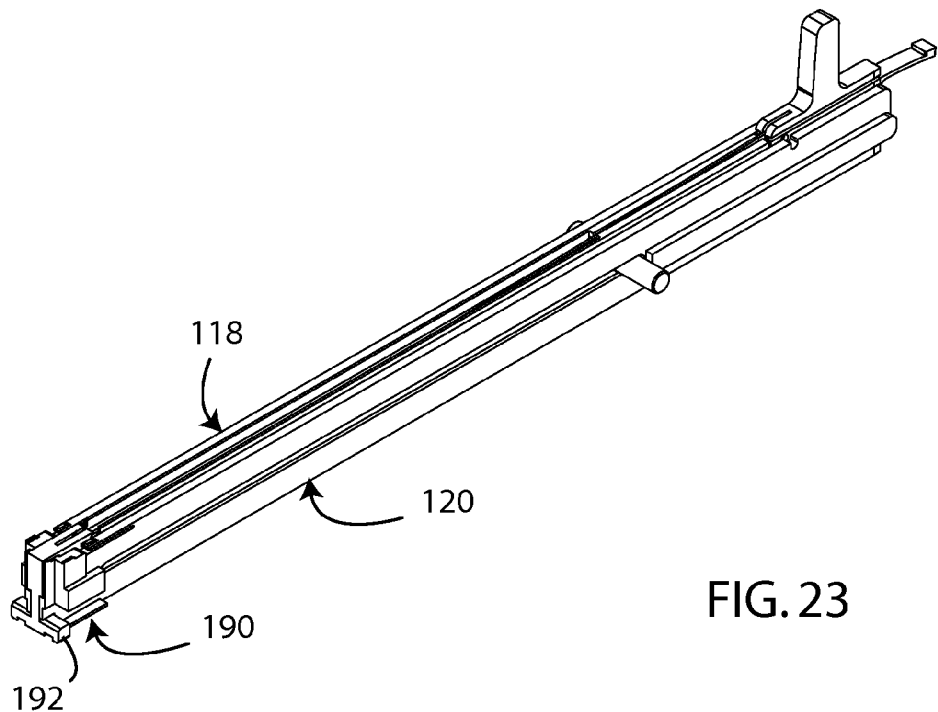
FIG. 23 is a perspective view of the wedge assembly, knife insert and knife of FIG. 22.

The wedge assembly 100 may include one or more outriggers 114 that extend outward at least partially laterally. At least one outrigger 114 is sized to contact the interior of a side wall of the staple holder 12. Advantageously, both outriggers 114 contact the interior of a side wall of the staple holder 12. Such engagement positions the wedge assembly 100 at a substantially constant lateral position within the staple holder 12 as it slides therein, and prevents canting of the wedge assembly 100 within the staple holder 12 during its travel therein. "Canting" refers to undesired motion about an axis of the wedge assembly 100 that would cause the wedge assembly 100 to experience increased friction or to jam within the staple holder 12. Referring also to FIGS. 17 and 23, a pin slot 121 may extend longitudinally along each lateral side of the staple holder 12. The clamp pin 30 may be received through the pin slots 121, such that the pin slots 121 allow the wedge assembly 100 to slide relative to the clamp pin 30 without interference therefrom. Alternately, the wedge assembly 100 may be free to slide relative to the clamp pin 30 in any other suitable manner, and one or more pin slots 121 may be omitted from the staple holder 12.

A slot 116 may extend longitudinally along at least a part of the wedge assembly 100, and may be substantially laterally centered in the wedge assembly 100. The wedge assembly 100 thereby may be bifurcated, such that it includes a right arm 118 and a left arm 120 spaced apart from one another. Alternately, the wedge assembly 100 need not be completely bifurcated. One or more wedges 122 may be located at or near the distal end of the wedge assembly 100, on an upper surface thereof. Advantageously, two wedges 122 are positioned in proximity to the distal end of each arm 118, 120. The wedges 122 on each arm 118, 120 may be staggered longitudinally. As used in this document with respect to wedges 122, "longitudinally staggered" means that one wedge 122 on one arm 118, 120 is positioned at a different location longitudinally on that arm 118, 120 than another wedge 122 on the same arm 118, 120. The wedges 122 may be longitudinally staggered a distance substantially equal to the longitudinal stagger of staples on a corresponding feeder belt, as set forth in greater detail below. Each wedge 122 is configured to deform and then shear one or more staples from a feeder belt, as set forth in U.S. patent application Ser. No. 12/400,790, filed Mar. 9, 2009, and U.S. patent application Ser. No. 11/851,379, filed Sep. 6, 2007 (the "Endocutter Documents"), both of which are hereby incorporated by reference in their entirety. The wedges 122 may be shaped substantially as set forth in the Endocutter Documents, or may be shaped in any other suitable manner. One or more wedges 122 may be located at a different position on the wedge assembly 100, if desired.

Figure 19:
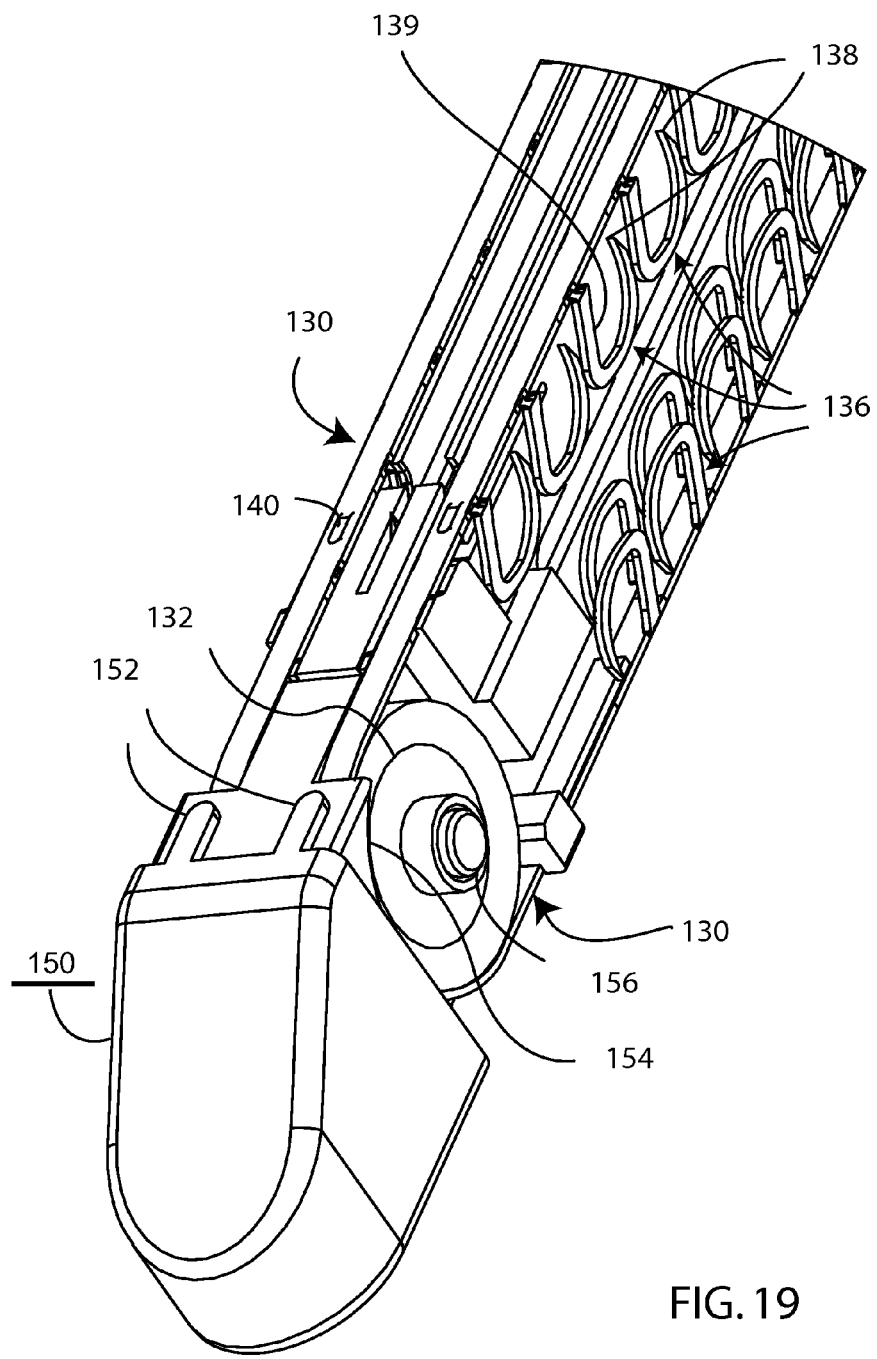
FIG. 19 is a perspective cutaway view of the distal end of the exemplary staple holder assembly of FIG. 12, showing the feeder belts.
Figure 20:
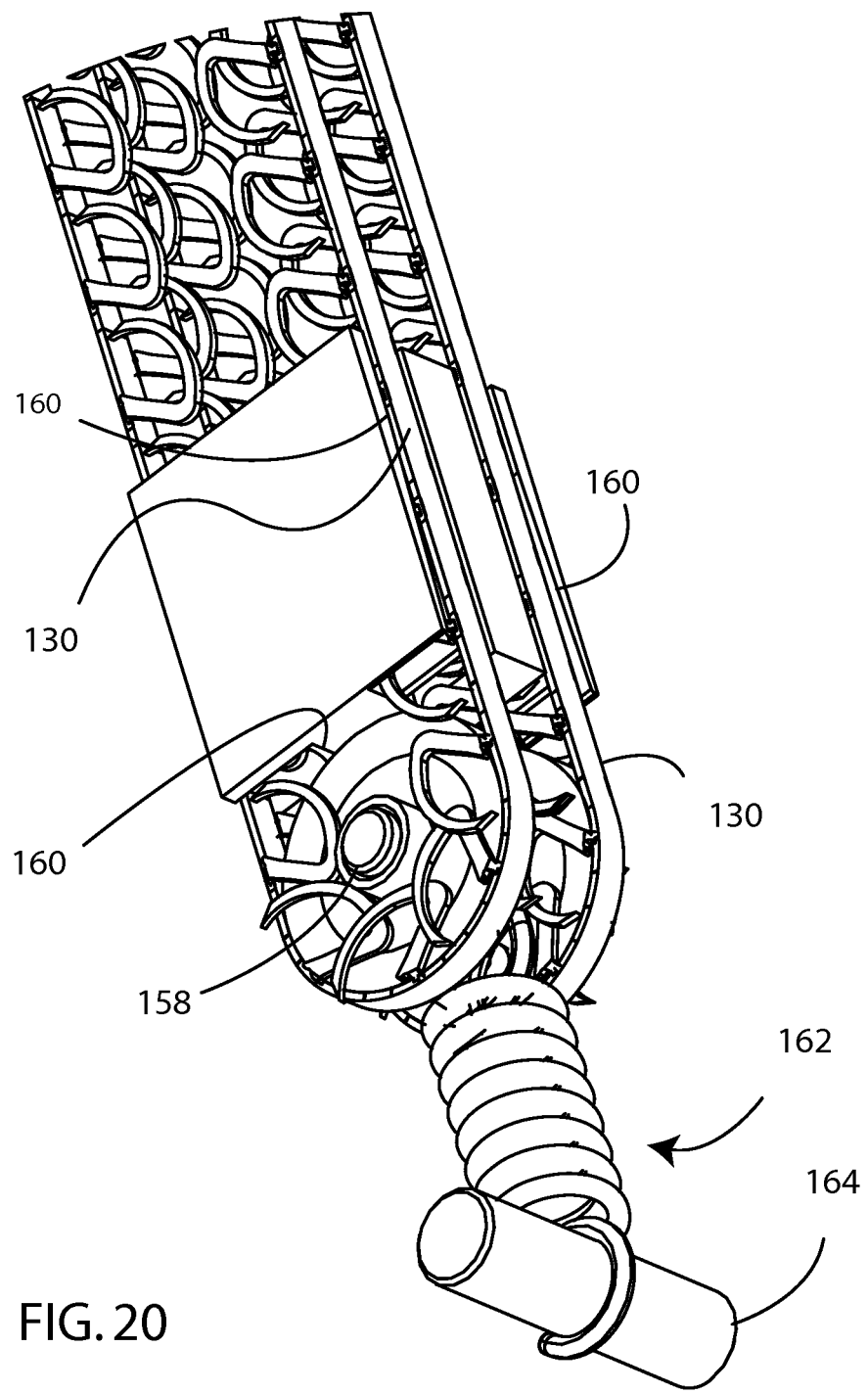
FIG. 20 is a perspective cutaway view of the proximal end of the exemplary staple holder assembly of FIG. 12, showing the feeder belts.
Figure 21:
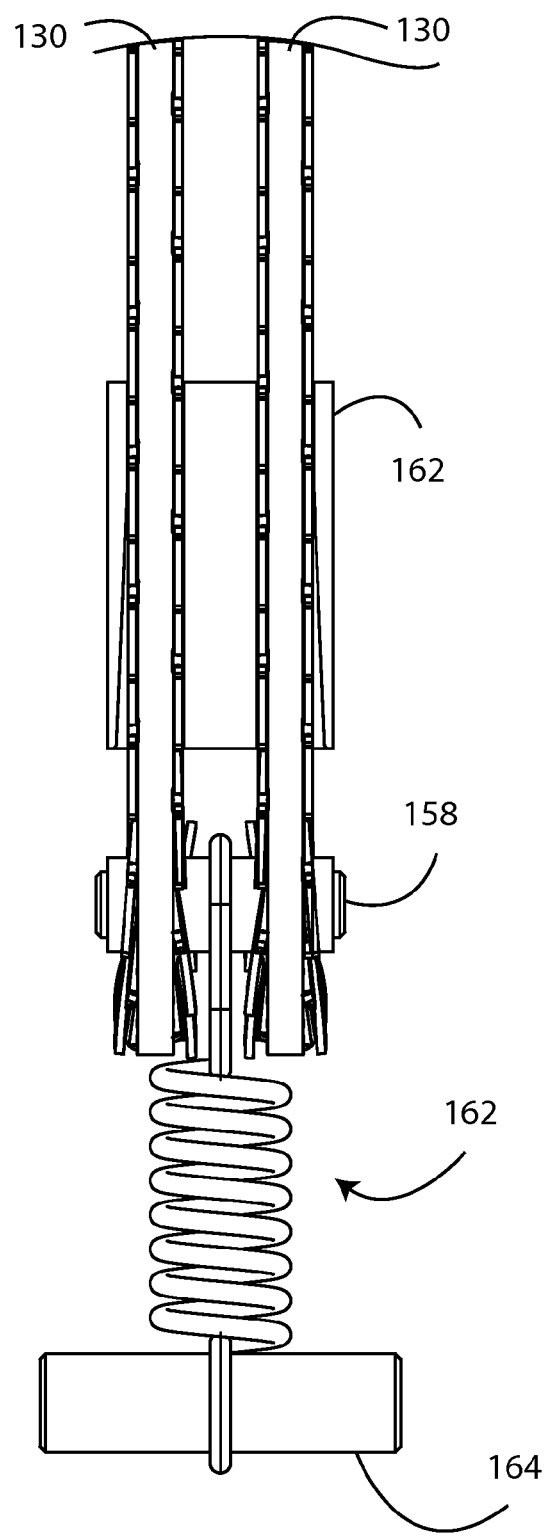
FIG. 21 is a top cutaway view of the distal end of the exemplary staple holder assembly of FIG. 12, showing the feeder belts.

Referring to FIGS. 19-21, one or more feeder belts 130 may be positioned within the staple holder 12. Each feeder belt 130 may be configured as set forth in the Endocutter Documents. Each feeder belt 130 may be a long, narrow, thin strip of material from which one or more staples 136 extend. Each feeder belt 130 may be fabricated from stainless steel, nickel-titanium alloy, or any other suitable metallic or non-metallic material. Each feeder belt 130 may be flexible enough, and strong enough, to be advanced linearly and then redirected around a distal wheel 132 and a proximal wheel 134, each wheel 132, 134 being mounted in the staple holder 12. Advantageously, each feeder belt 130 may be a continuous loop that extends around both wheels 132, 134. Alternately, one wheel 132, 134 may be omitted, and the feeder belt 130 is fed about the remaining wheel in a suitable direction. If so, the feeder belt 130 need not be a continuous loop. At least one staple 136 may be separably fixed to each feeder belt 130. Each staple 136 may be shaped in any suitable manner; the staples 136 may be shaped substantially the same as one another, or may be shaped differently. As one example, each staple 136 may be generally V-shaped, with a free end 138 that may be characterized as a tissue penetrating tip 138. The other end 139 of the staple 136 may be separably connected to the feeder belt 130. Advantageously, each staple 136 is frangibly connected to the feeder belt 130. The separable connection between at least one staple 136 and the corresponding feeder belt 130 is set forth in the Endocutter Documents. Thus, one end 139 of the staple 136 may be fixed to the feeder belt 130 and the other end 138 of the staple 136 may be free.

Alternately, the staple 136 may be shaped in any other suitable manner. The staples 136 may be connected to the feeder belt 130 in any suitable orientation. As one example, one or more of the staples 136 are oriented generally parallel to the longitudinal centerline of the feeder belt 130. That is, one or more of the staples 136 each may lie in a plane that is generally parallel to the longitudinal centerline of the feeder belt 130. The staples 136 may be attached to or in proximity to at least one lateral edge of the corresponding feeder belt 130, such that staples 136 may form a generally longitudinally-extending row along at least one lateral edge of at least one feeder belt 130. Alternately, at least one row of staples 136 may extend longitudinally along a line between the lateral edges of the corresponding feeder belt 130. As another example, one or more of the staples 136 each may be oriented in a direction angled relative to the longitudinal centerline of the feeder belt 130. As another example, the staples 136 each may be oriented in a direction angled relative to the transverse direction, which is the direction perpendicular to the longitudinal centerline of the feeder belt 130.

Staples 136 in two or more different rows along a single feeder belt 130 may be arranged in any suitable manner relative to one another. As one example, staples 136 in two or more different rows along a single feeder belt 130 may be longitudinally staggered relative to one another. That is, at a given longitudinal position along a single feeder belt 130 at which a staple 136 in one row is attached to the feeder belt 130, at least one other row does not have a staple 136 attached to that feeder belt 130. Alternately, staples 136 in two or more of the rows along a single feeder belt 130 may be aligned with one another, along at least part of the length of the rows, such that at a given longitudinal position along the feeder belt 130 at which a staple 136 in one row is attached to the feeder belt 130, each other row has a staple 136 attached to the feeder belt 130 as well. Alternately, staples 136 in two or more rows along a single feeder belt 130 may be arranged differently along different longitudinal portions of that feeder belt 130. Staples 136 may be arranged relative to one another in the same manner, or differently, on different feeder belts 130 of the linear cutter 2. The staples 136 in each row may be substantially evenly spaced apart from one another. That is, the distance between any two longitudinally-adjacent staples 136 in a row may be substantially the same. Alternately, at least two longitudinally-adjacent staples 136 in each row may be spaced apart a distance different from the distance between two other longitudinally-adjacent staples 136.

At least one aperture 140 may be defined in at least one feeder belt 130. Each aperture 140 may be generally rectangular, or have any other suitable shape. Each aperture 140 may be defined completely through the feeder belt 130, or defined partially through it. The apertures 140 may be shaped and sized the same as one another, or differently, as desired. The apertures 140 are configured to be engaged by corresponding latch bumps 142, each defined on a latch cantilever 144 on an upper surface of the wedge assembly 100. Advantageously, each arm 118, 120 has a separate latch cantilever 144 associated with it. Each latch bump 142 and latch cantilever 144 acts to advance the corresponding feeder belt 130 after a firing, as described in greater detail below. The advancement of the feeder belt 130 using a latch may be substantially as set forth in U.S. patent application Ser. No. 12/436,101, filed on May 5, 2009, which is hereby incorporated by reference in its entirety. The latch cantilevers 144 may be biased upward to urge the latch bumps 142 into the corresponding apertures 140 in the feeder belts 130.

A nosepiece 150 may be connected to the distal end of the staple holder 12. The nosepiece 150 optionally may be color-coded to match the size of the staples 136 held by the staple holder 12. The relationship between size of staples 136 and color coding is standard in the art. The nosepiece 150 may include one or more raised areas 152 configured to be received in the notches 92 at the distal end of the staple holder 12. Engagement between those raised areas 152 and the notches 92 may provide additional torsional stability to the staple holder 12. The nosepiece 150 may include at least one feeder belt guide 154 defined on an inner surface thereof. The feeder belt guide 154 may be curved about substantially the same radius of curvature as the distal wheel 132, and may be spaced apart from the distal wheel 132 a distance slightly greater than the thickness of the feeder belt 130 received about the distal wheel 132. Alternately, the feeder belt guide 154 may be shaped or curved differently, and/or may be spaced apart from the distal wheel 132 a different distance. Advantageously, the feeder belt guide 154 extends substantially along sixty degrees of the distal wheel 132. Where the feeder belt guide 154 extends along that degree of curvature, the feeder belt guide 132 is sufficiently long to assist in directing the motion of the feeder belt 130 about the distal wheel 132, and short enough to minimize friction between the feeder belt 130 and the feeder belt guide 154. However, the feeder belt guide 154 may extend in an arc of any desired length about the distal wheel 132.

Figure 12:
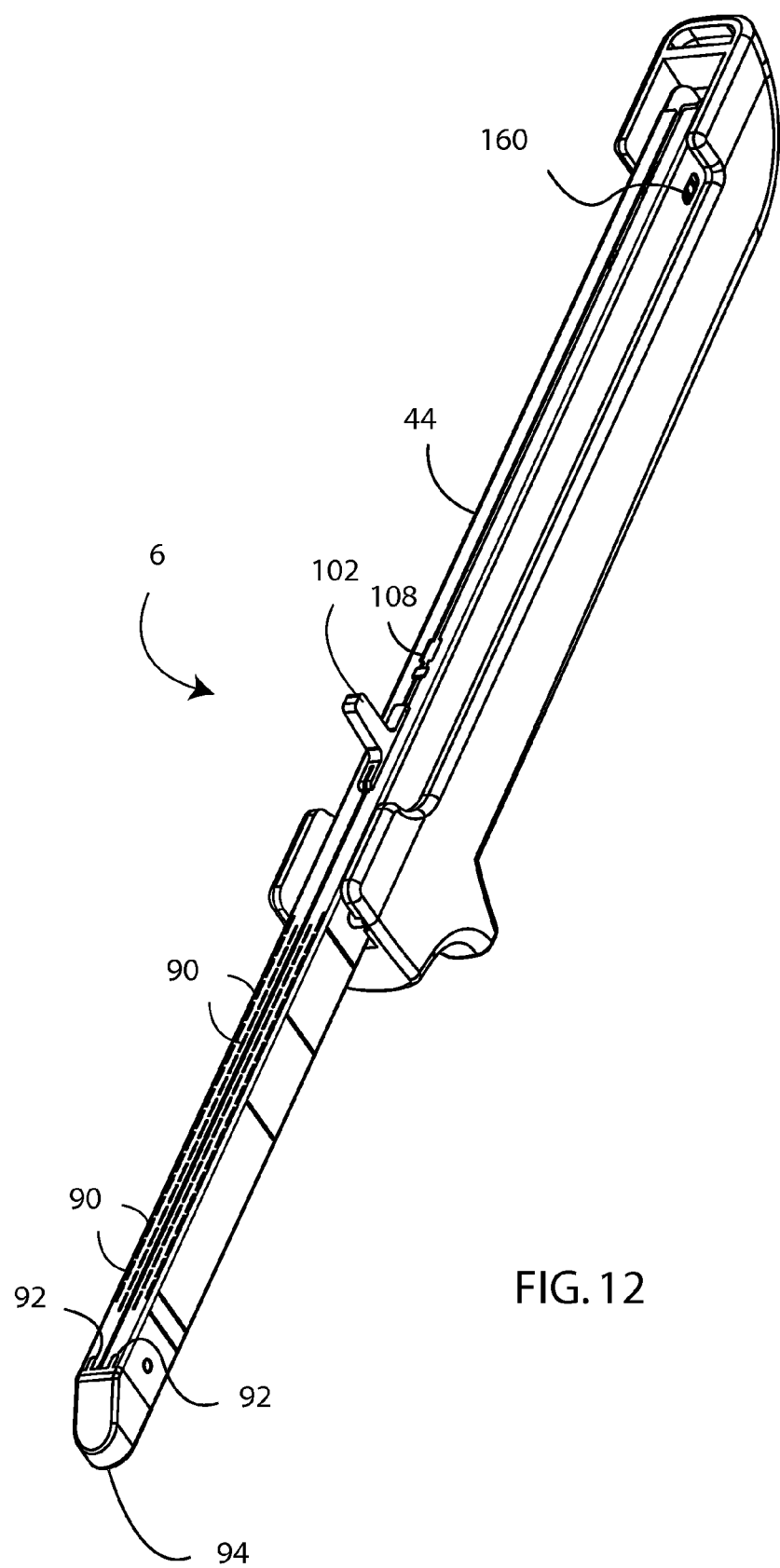
FIG. 12 is a perspective view of an exemplary staple holder assembly of the linear cutter of FIG. 1.
Figure 13:
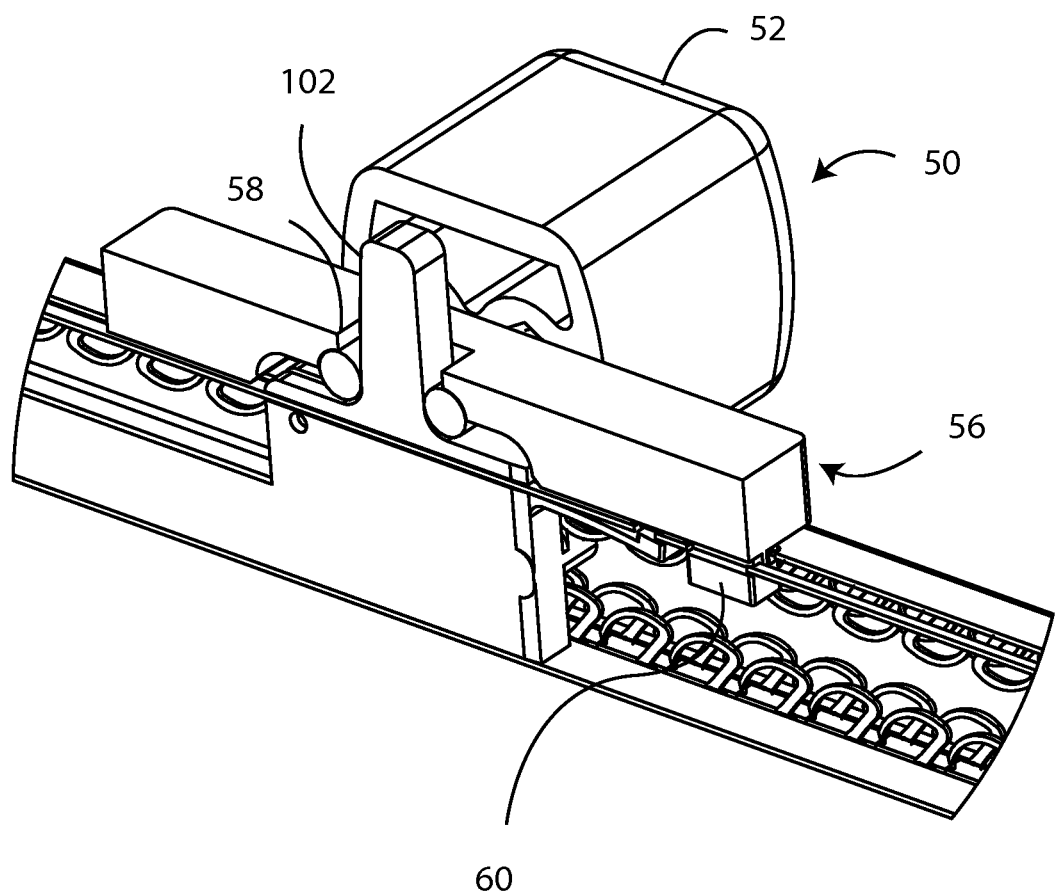
FIG. 13 is a detail cross-section view of the engagement between the deployment handle of FIG. 7 and the exemplary staple holder assembly of FIG. 12, in the closed position.
Figure 14:
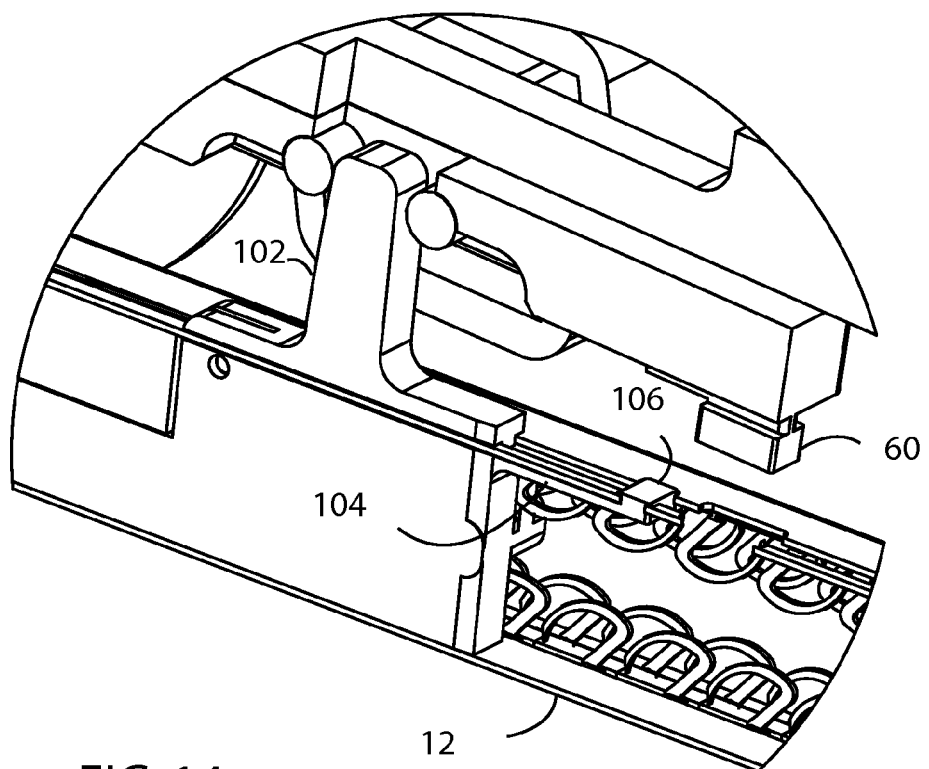
FIG. 14 is a detail cross-section view of the engagement between the deployment handle of FIG. 7 and the exemplary staple holder assembly of FIG. 12, in the open position.
Figure 15:
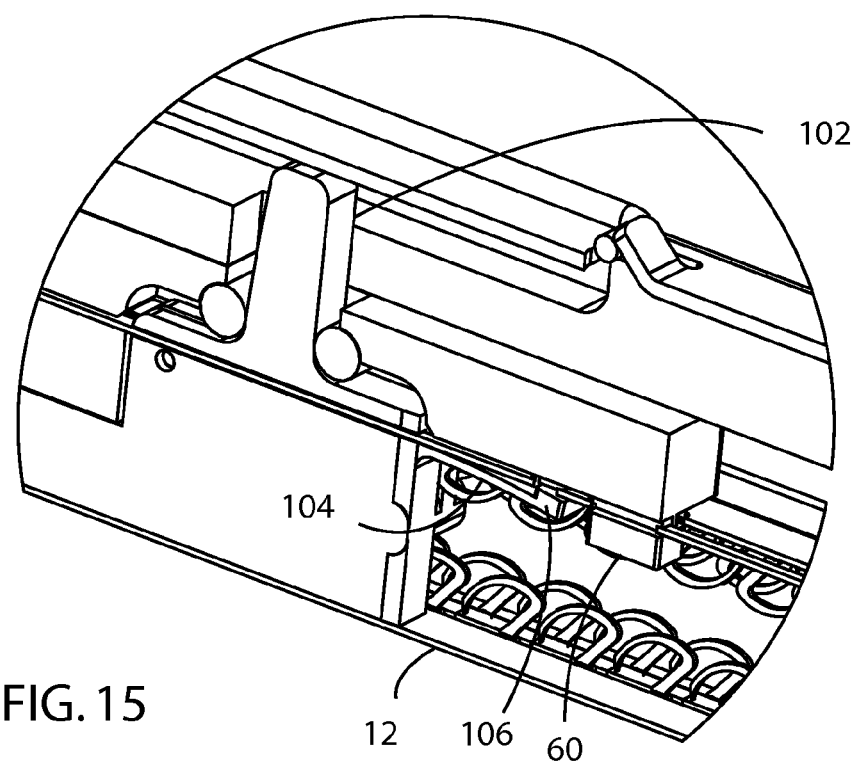
FIG. 15 is a detail cross-section view of the engagement between the deployment handle of FIG. 7 and the exemplary staple holder assembly of FIG. 12, in the closed position.
Figure 16:
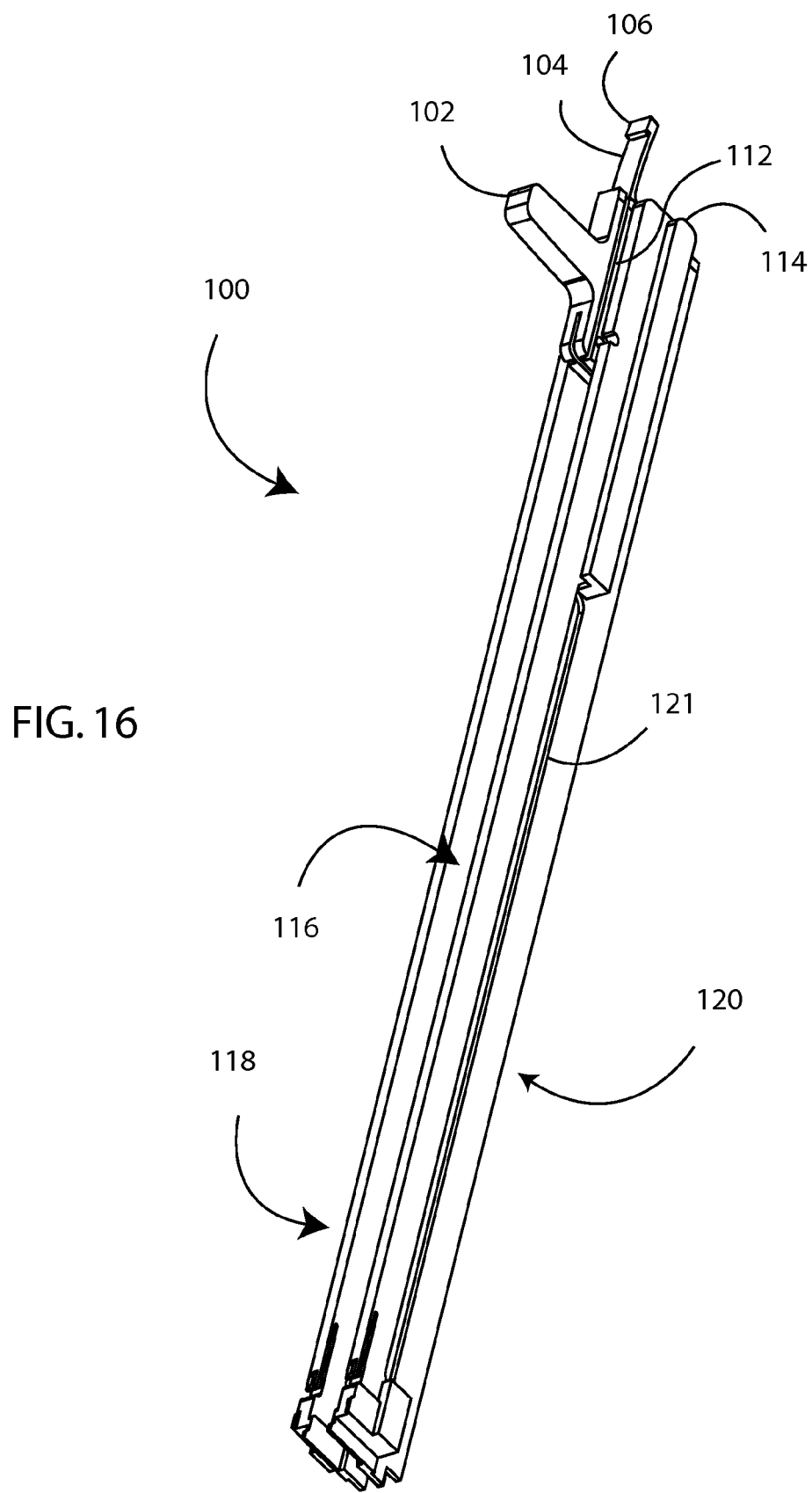
FIG. 16 is a perspective view of an exemplary wedge assembly slidable within the exemplary staple holder assembly of FIG. 12.

Each distal wheel 132 and each proximal wheel 134 may be connected to the staple holder 12 in any suitable manner. As one example, the distal wheel or wheels 132 are mounted to a distal axle 156 that in turn is mounted to apertures (not shown) in the lateral sides of the staple holder 12. The distal axle 156 may be fixed to the staple holder 12, and each distal wheel 132 may be rotatable about that distal axle 156. Alternately, the distal axle 156 may be free to rotate relative to the staple holder 12, and each distal wheel 132 may be either fixed to the distal axle 156 or free to rotate about the distal axle 156. The proximal wheel or wheels 134 may be mounted in a similar manner to a proximal axle 158. The proximal axle 158 may be tensioned to a force, to ensure that the feeder belt or belts 130 maintain a desired level of tension. Referring also to FIG. 12, a proximal axle slot 160 may be defined through each lateral side of the staple holder 12. The proximal axle slot 160 may be oriented generally longitudinally relative to the staple holder 12, or may be oriented differently. The proximal axle slot 160 may be substantially linear, or may be curved or otherwise shaped if desired. The proximal axle 158 may be received in the proximal axle slots 160, and may be slidable within those slots 160. Referring also to FIGS. 20-21, a spring 162 may be attached at one end to the proximal axle 158, and at the other end to a pin 164 that in turn is fixed to the staple holder 12. Alternately, the spring 162 may be attached directly to the staple holder 12, or otherwise fixed to the staple holder 12. The pin 164 may be located proximal to the proximal axle 158. The spring 162 may exert a substantially constant force in the proximal direction on the proximal axle 158. That force may be substantially equal to the tensioning force applied in turn by the proximal wheel or wheels 134 on the corresponding feeder belt or belts 130. In this way, the spring 162 may be used to create a desired amount of tension in the feeder belt or belts 130 in the staple holder 12. The spring 162 may be a coil spring or any other suitable spring, or may be a plurality of springs. Alternately, the proximal axle 158 may be attached to the staple holder 12 in the same manner as the distal axle 156. Alternately, the distal axle 156 may be tensioned relative to the staple holder 12 instead of, or in addition to, the proximal axle 158; if so, the distal axle 156 may be tensioned in substantially the same manner as described in this paragraph.

At least one feeder belt 130 may include staples 136 that are located at a position thereon in which those staples 136 may be moved around one of the wheels 132, 134 as the feeder belt 130 advances. Accommodation for motion of staples 136 about at least one of the wheels 132, 134 may be accomplished in any suitable manner. As one example, at least one wheel 132, 134 has a diameter greater than twice the height of the staples 136. In this way, there is no interference between staples 136 connected to an upper portion of the feeder belt 130 and staples 136 on a lower portion of the feeder belt 130. Advantageously, at least one of the wheels 132, 134 is greater in diameter than twice the height of the staples 136 plus the diameter of the axle 156, 158 corresponding to that wheel 132, 134, such that the axle 156, 158 does not interfere with the staples 136 as they are advanced about the corresponding wheel 132, 134 as a result of motion of the corresponding feeder belt 130. As another example, the staples 136 may be canted before encountering at least one of the wheels 132, 134. "Canting" in this context refers to the rotation of a staple 136 relative to the feeder belt 130 about its yaw axis. The yaw axis is the axis of the staple 136 that extends perpendicular to a plane tangent to the feeder belt 130 at any given point, and that extends through the connection between that staple 136 and the feeder belt 130. In this way, referring in particular to FIG. 21, the staples 136 may be canted outward as they rotate about a wheel 132, 134. As a result of this canting, the staples 136 do not interfere with one another as the feeder belt 130 pulls them around a wheel 132, 134. In this way, the upper portion and lower portion of the feeder belt 130 may be spaced apart a distance less than twice the height of the staples 136, and at least one wheel 132, 134 may have a diameter less than twice the height of the staples 136. Canting the staples 136 approximately nine degrees prevents interference of the staples 136 with one another as they travel about a wheel 132, 134. However, the staples 136 may be canted a greater or lesser amount, which may change based on the diameter of at least one wheel 132, 134: the smaller the diameter of a wheel 132, 134, the more canting of staples 136 may be necessary. Canting of the staples 136 may be performed in any suitable manner. As one example, staples 136 may be canted by pulling them through a slot 160 in a straightener 162. The slot 160 may begin with a cross-section in alignment with the staples 136, then angle progressively outward such that contact between each staple 136 and the angled slot 160 causes each staple 136 to cant outward at an angle related to the exit angle of the slot 160. Such a straightener 162 may be as described in U.S. Provisional Patent Application Ser. No. 61/435,912, filed on May 5, 2009, which is hereby incorporated by reference herein in its entirety. Similarly, the straightener 162 may include a slot 160 on its opposite site that is substantially the mirror image of the slot 160 through which the staples 136 were previously pulled, where that slot 160 is initially angled to match the cant of the staples 136, then angles progressively inward to be substantially perpendicular to the feeder belt 130, causing the staples 136 to move inward to a degree where they are no longer canted. Alternately, the staples 136 may remain in a canted state after they have rotated about at least one wheel 132, 134. Alternately, the staples 136 are fabricated in a canted alignment with the corresponding feeder belt 130, such that at least one slot 160 may be eliminated, and such that the straightener or straighteners 162 may be omitted.

Figure 22:
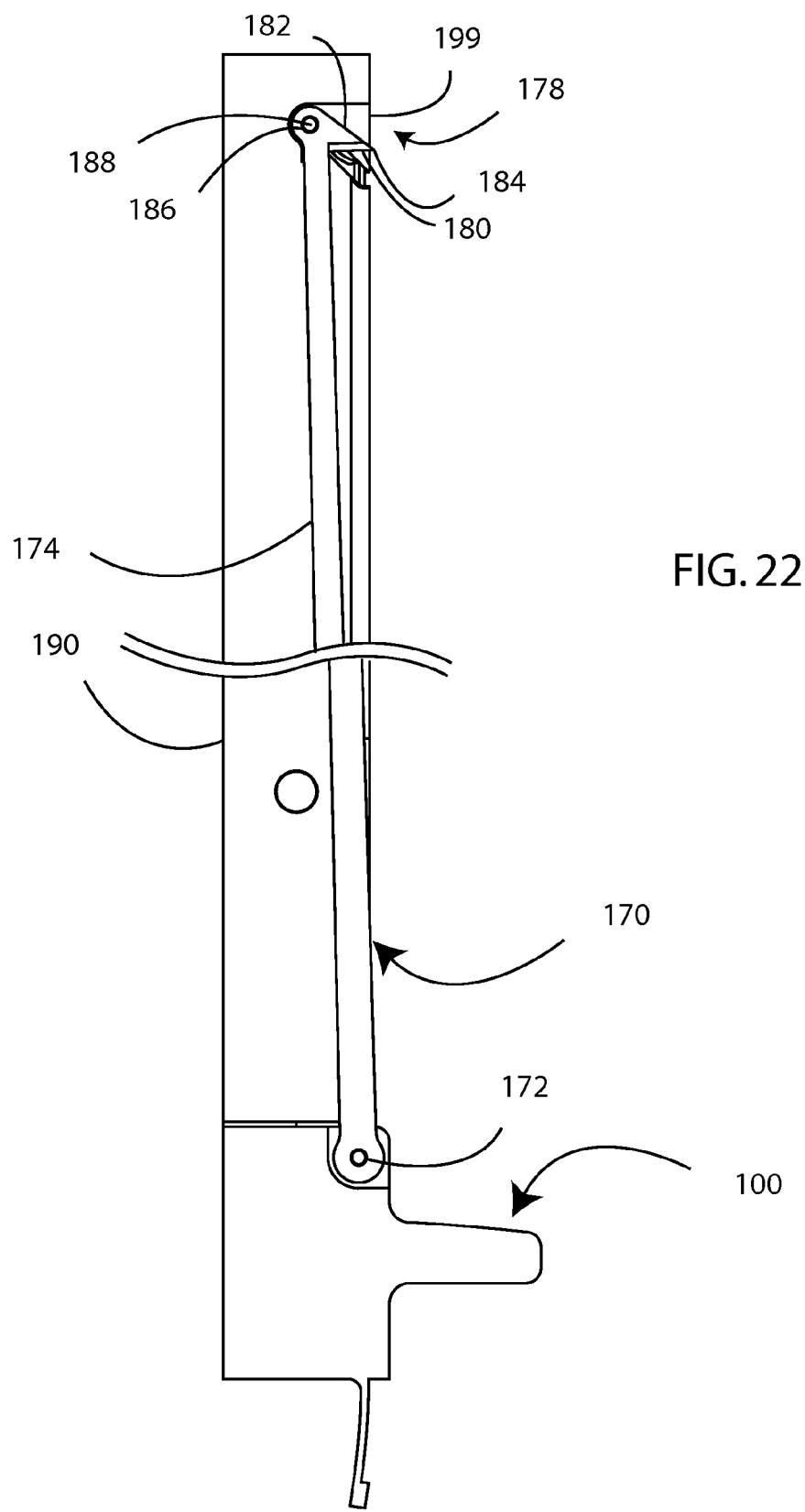
FIG. 22 is a cross-section view of the exemplary wedge assembly of FIG. 16, a knife insert, and a knife.
Figure 24:
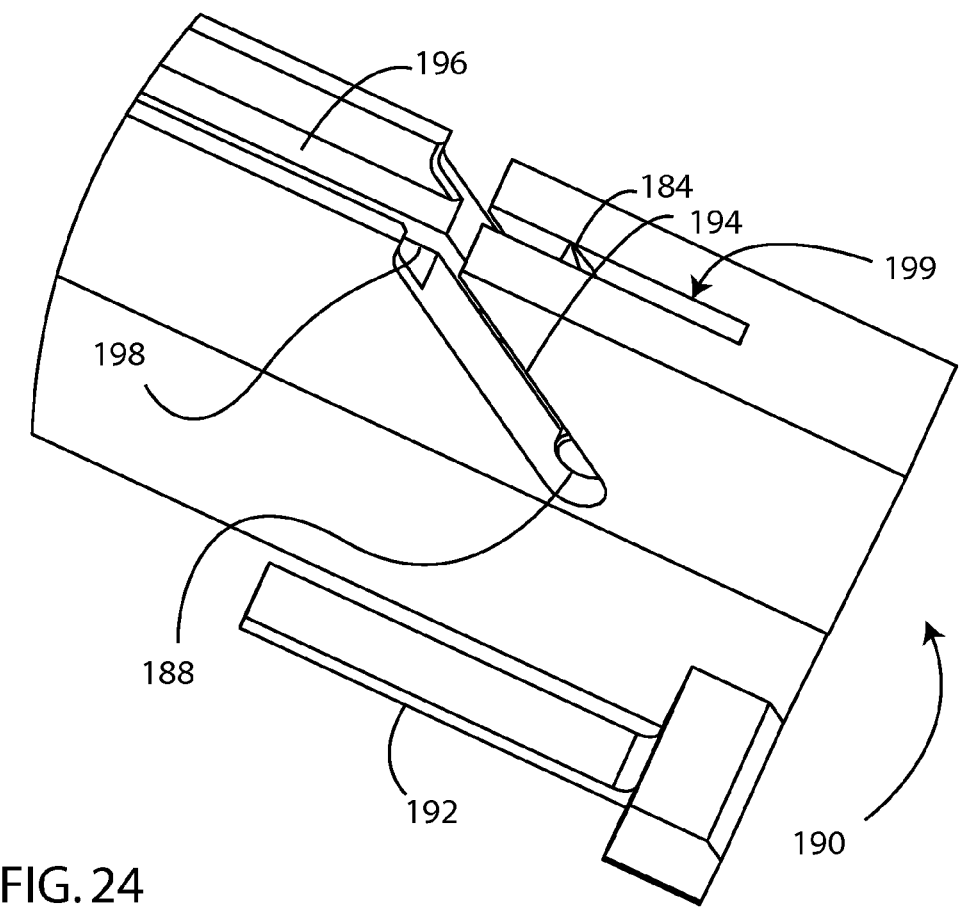
FIG. 24 is a detail perspective view of the wedge assembly, knife insert and knife of FIG. 22.

Referring also to FIGS. 22-24, a knife assembly 170 may be connected to the wedge assembly 100. The wedge assembly 100 may include at least one pivot pin 172 defined therein. The knife assembly 170 may include a longitudinally-extending knife arm 174 with an aperture 176 at its proximal end through which the pivot pin 172 is received, such that the knife assembly 170 can rotate about the pivot pin 172. Alternately, the knife arm 174 may be oriented differently, or otherwise connected to the wedge assembly 100. Alternately, the aperture 176 may be located at a different position along the knife assembly 170. The knife assembly 170 may be substantially flat and thin, and may be fabricated from a single piece of sheet metal. Alternately, the knife assembly 170 may be configured and/or fabricated differently. A knife 178 may be positioned at or near the distal end of the knife assembly 170. Alternately, the knife 178 may be positioned different on the knife assembly 170. The knife 178 may be substantially teardrop-shaped, with a sharp proximal edge 180, a blunt distal edge 182, and a sharp point 184 oriented upward and located at or near the junction between the sharp proximal edge 180 and the blunt distal edge 182. Alternately, the knife 178 may be shaped or configured differently. The knife 178 may include an aperture 186 through which a guide pin 188 is received.

A knife insert 190 may be positioned within the staple holder 120. The knife insert 190 may be fixed to or fixed relative to the staple holder 120, or may be slidable within the staple holder 120. The knife insert 190 may be configured such that the majority thereof is held between the arms 118, 120 of the bifurcated wedge assembly 100. Alternately, the knife insert 190 may be configured differently. The knife insert 190 may include one or more outriggers 192 at or near its distal end, extending at least partially in the lateral direction. Such outriggers 192 may be used to attach the knife insert 190 to the staple holder 12, and/or to stabilize it within the staple holder 120. Alternately, outriggers 192 may be located at a different position on the knife insert 190, or may be omitted. An angled guide slot 194 may be defined in the knife insert 190 at or near its distal end. Alternately, the guide slot 194 may be defined in a different location on the knife insert 190. The guide slot 194 may be substantially linear, and may slope upward toward the proximal direction. Alternately, the guide slot 194 may be shaped and/or oriented differently. A knife travel platform 196 may be defined within the knife insert 190, lower than the upper surface of the knife insert 190, and may be oriented generally longitudinally. As the wedge assembly 100 moves proximally, the guide pin 188 rides up the guide slot 194. The knife travel platform 196 is located proximal to the guide slot 194, such that as the wedge assembly 100 continues to move proximally, the guide pin 188 continues to travel along the surface of the knife travel platform 196. In this way, the guide slot 194 and knife travel platform 196 both support and guide the guide pin 188, and thereby the travel of the knife 178, as the wedge assembly 100 moves proximally. A slot 198 may be defined in the knife travel platform 196 to accommodate the portion of the knife 178 that extends below the guide pin 188. Alternately, the bottom of the knife 178 may engage the surface of the knife travel platform 196, instead of the guide pin 188. The knife insert 190 includes a knife pocket 199 defined therein that is sized to hold the entirety of the knife 178 in the initial position.

Operation

An opening is made in the body of the patient to allow access to the thoracic cavity, abdominal cavity or any other cavity or interior space. At least the effector 16 of the linear cutter 2 is then introduced into the body of the patient through that opening. The effector 16 is positioned by the user at a surgical site, such as across a segment of large intestine or a portion of the stomach. For clarity, this document describes the operation of the linear cutter 2 for transection of a segment of intestine. However, the use of the linear cutter 2 is not limited to blood vessel transection; the linear cutter 2 may be used to perform any other suitable procedure at any other surgical site in the body. For example, the linear cutter 2 may be used to transect vascular tissue or lung tissue.

Figure 3:
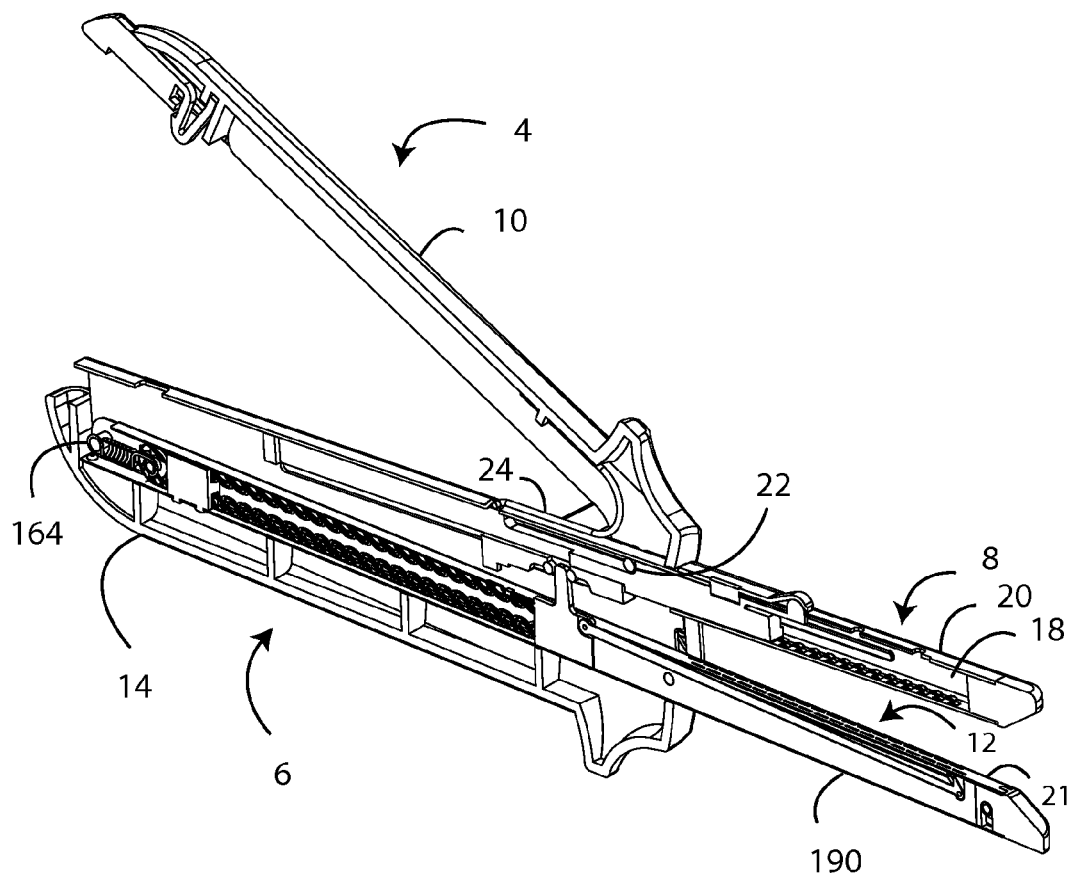
FIG. 3 is a perspective cross-section view of the exemplary linear cutter of FIG. 1 in the first, unclamped configuration.

Referring to FIGS. 1, 3 and 4, at least the distal end of the anvil 8 is initially spaced apart from the staple holder 12, such that the effector 16 is open. If the effector 16 is initially closed upon insertion into the patient, the effector 16 is first opened to the open position; such opening is described in greater detail below. The end effector 4 is advanced over the intestinal segment to be transected, until the entire diameter of the intestinal segment is located between the anvil 8 and the staple holder 12. Advantageously, the intestinal segment is oriented substantially at a right angle to the anvil 8 and the staple holder 12. However, the intestinal segment may be oriented at any other suitable angle relative to the anvil 8 and the staple holder 12.

Referring also to FIGS. 9-11, the adjustable tissue stop 70 may then be adjusted, if desired by the user. Alternately, the adjustable tissue stop 70 may be adjusted before receiving the intestinal segment in the effector 16. Alternately, the adjustable tissue stop 70 may be adjusted both before and after receiving the intestinal segment in the effector 16 between the anvil 8 and the staple holder 12. To adjust the adjustable tissue stop 70, the user first depresses the finger piece 82 downward. Such motion depresses the protrusion 72, thereby flexing the distal end of the cantilever 76 downward. The latch 78 attached to the cantilever 76 and/or protrusion 72 is thereby moved downward as well, out of engagement with the corresponding latching slot 80 on the upper surface of the anvil 8. The adjustable tissue stop 70 is then free to slide along the anvil 8. The user may slide the adjustable tissue stop 70 such that the intestinal segment is positioned between a stop piece 200 of the adjustable tissue stop 70 and a marking 202 on the staple holder 12. The stop piece 200 may extend lateral to at least one side of the anvil 8, and is located relative to the remainder of the adjustable tissue stop 70 such that it defines one end of the adjustable staple line. The marking 202 on the staple holder 12 may be a line or any other demarcation on the staple holder 12 that defines the other end of the adjustable staple line. Advantageously, the adjustable tissue stop 70 is adjusted such that the distance between the stop piece 200 is slightly greater than the width of the intestinal segment engaged by the effector 16. The adjustable tissue stop 70 is slid until the appropriate staple line length is selected, and then the user ceases to depress the finger piece 82 downward when the latch 78 is positioned under the appropriate latching slot 80 on the upper surface of the anvil 8. Alternately, the user may cease depressing the finger piece 82 and continue to slide the adjustable tissue stop 70 until each latch 78 snaps back up into the appropriate latching slot 80; the latch or latches 78 are biased upward by the cantilever 76, such that motion of the latch or latches 78 into the same longitudinal location as a latching slot 80 causes the latch or latches 78 to move upward into that latching slot 80.

The effector 16 is then closed in any suitable manner. As one example, the user squeezes the handle grips 10, 14 together. As the first handle grip 10 of the anvil assembly 4 is squeezed toward the second handle grip 14 of the staple holder assembly 6, the user exerts an amount of force sufficient to overcome the biasing force exerted by the wire 24 or other mechanism that biases the first handle grip 10 upward away from a remainder of the anvil assembly 4. Referring also to FIGS. 4-5, as the first handle grip 10 of the anvil assembly 4 is compressed toward the second handle grip 14, the forks 26 at the distal end of the first handle grip 10 move relative to the clamp pins 30 that extend laterally from the staple holder 12, one from each side thereof. As the first handle grip 10 is compressed downward and rotates about the pin 22, each clamp pin 30 is grabbed by the corresponding fork 26, entering the slot 28 at the distal end of each fork 26. The slots 28 are shaped such that continuing rotary motion of the first handle grip 10 about the pin 22 causes the forks 26 to lift up the corresponding pins 22 and/or pull down the anvil 8, thereby moving the anvil assembly 4 relative to the staple holder assembly 6 as seen in FIG. 5.

Referring also to FIG. 3, as the handle grips 10 are closed together, the anvil assembly 4 may pivot about the pin 164, which may be fixed to the staple holder assembly 6. The anvil assembly 4 may include a U-shaped detent (not shown) that is sized and shaped to engage the pin 164 such that the anvil assembly 4 pivots about the pin 164 as the anvil assembly 4 moves closer to the staple holder assembly 6. Alternately, the anvil assembly 4 may pivot about a different point on the staple holder assembly 6, or otherwise move toward the staple holder assembly 6. As the anvil assembly 4 moves toward the staple holder assembly 6, the living hinge 36 of the clamp latch 32, or other component of the clamp latch 32, moves toward the clamp slot 42 defined on the upper surface of the staple holder 12. As the living hinge 36 moves into the clamp slot 42, contact between the proximal end of the clamp slot 42 and the living hinge 36 compresses that living hinge 36 distally. This compression continues as the living hinge 36 moves far enough into the clamp slot 42 that the living hinge 36 snaps back proximally, such that the ledge 40 moves underneath the proximal end of the clamp slot 42. The ledge 40 prevents the first handle grip 10 from rotating back upward about the pin 22, because it engages the upper surface 44 of the staple holder 12 proximal to the clamp slot 40.

As the anvil assembly 4 closes toward the staple holder assembly 6, the effector 16 clamps the intestinal segment held between the anvil 8 and staple holder 12. The actuation of the linear cutter 2 clamp the tissue to be treated may be referred to as clamping. As the anvil assembly 4 closes toward the staple holder assembly 6, the deployment handle 50 moves into engagement with the engagement feature 102 of the wedge assembly 100. As one example, the rods 54 in the aperture 58 of the deployment handle 50 are spaced apart from one another substantially the same distance as the dimension of the engagement feature 102, such that the rods 54 engage the proximal and distal surfaces of the engagement feature 102 as the anvil assembly 4 closes toward the staple holder assembly 6. When the linear cutter 2 has reached the clamped position, the rods 54 may be positioned at or near the base of the engagement feature 102. As another example, the proximal and distal surfaces of the aperture 58 engage the proximal and distal surfaces of the engagement feature 102. When the linear cutter 2 has reached the clamped position, the proximal and distal edges of the aperture 58 may be positioned at or near the base of the engagement feature 102. Alternately, the engagement feature 102 may be provided on the deployment handle 50, and the rods 54 and/or aperture 58 may be defined in the wedge assembly 100. In this way, the engagement feature 102 moves downward into the aperture 58 in the wedge assembly 100, and is engages by rods 54 and/or the aperture 58 in substantially a mirror image of the manner described above.

Additionally, as the anvil assembly 4 moves toward the staple holder assembly 6, the primer 60 attached to the deployment block 50 contacts the brick 106 of the wedge assembly 100. Alternately, another feature attached to the deployment block 50 or to another portion of the anvil assembly 4 contacts the brick 106. Initially, the brick 106 resides at least partially in the brick receiving slot 108; this engagement prevents longitudinal motion of the wedge assembly 100 along the staple holder 12. The primer 60 is sized such that, as the anvil assembly 4 moves toward the staple holder assembly 6, the primer 60 pushes the brick 106 downward out of engagement with the brick receiving slot 108, thereby freeing the wedge assembly 100 relative to the staple holder 12. The knife 178 is initially held completely within the knife insert 190 in the knife pocket 199 or other location in the knife insert 190. Alternately, at least the sharp proximal edge 180 of the knife 178 is initially held completely within the knife insert 190.

Clamping is complete, the engagement feature 102 of the staple holder assembly 6 has engaged the anvil assembly 4, and the wedge assembly 100 has been freed for motion relative to the staple holder 12. The linear cutter 2 is now in the closed, clamped position, and is ready to deploy staples 136. In the closed, clamped position, before deploying the staples 136, the wedge assembly 100 is positioned such that the wedges 122 are distal to the staples 136 to be deployed, and the knife 178 is similarly positioned distal to the staples 136 to be deployed. The staples 136 are deployed, and tissue held in the effector 16 cut, in the direction from distal to proximal. Alternately, in the closed, clamped position, before deploying the staples 136, the wedges 122 and the knife 178 are positioned proximal to the staples 136 to be deployed, and those staples 136 are deployed and tissue held in the effector 16 cut in the direction from proximal to distal.

When the user is ready to actuate the tool (which may also be referred to as firing the tool), the user begins to slide the deployment handle 50 proximally, such as by grasping one or more grips 52 of the deployment handle 50 and pulling the grip or grips 52 proximally. Such actuation by moving the deployment handle 50 by hand may be referred to as manual actuation. Alternately, the deployment handle 50 may be actuated by a release of energy stored within the anvil assembly 4 or within another part of the linear cutter 2, or by release of energy supplied to the linear cutter 2 from an external source. Such actuation by the release or application of energy other than by hand may be referred to as powered actuation. As the deployment handle 50 slides proximally, it slides along the actuation slots 49 in the anvil 8, which may receive the rod or rods 54 therethrough. The actuation slots 49 constrain the motion of the deployment handle 50 along a direction in which the actuation slots 49 are oriented, which may be substantially longitudinal. Proximal motion of the deployment handle 50 drags the wedge assembly 100 proximally as well, due to engagement between the deployment handle 50 and the engagement feature 102 of the wedge assembly 100. Thus, the deployment handle 50, which is constrained for motion along the anvil 8 and need not enter the staple holder 12, drives motion of the wedge assembly 100 within the staple holder 12. That is, the anvil assembly 4 transmits force to the staple holder assembly 6, where that force moves the wedge assembly 100 and causes deployment of staples 136 and transection of tissue held in the effector 16.

Figure 18:
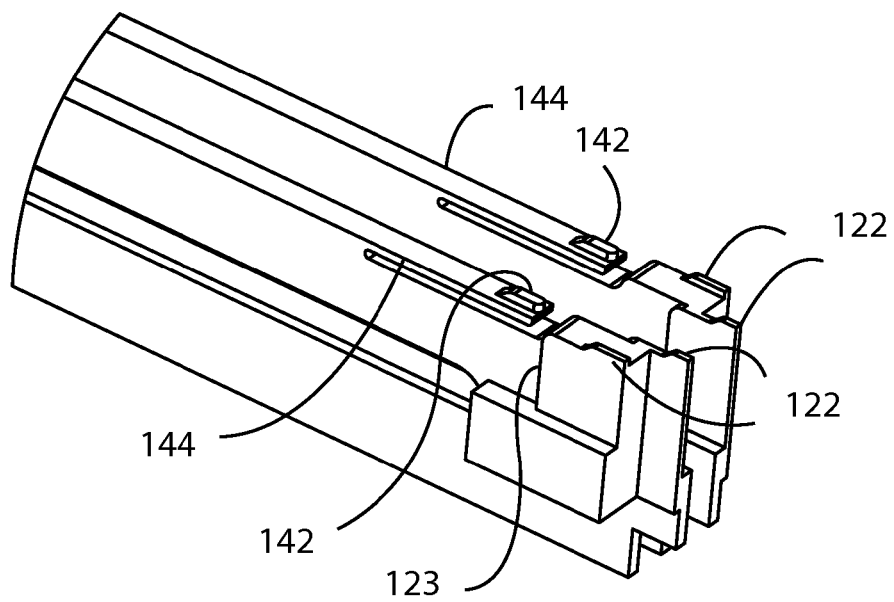
FIG. 18 is a detail perspective view of the distal end of the exemplary wedge assembly of FIG. 16.

Referring also to FIGS. 9 and 18-19, as the wedge assembly 100 moves proximally, the wedges 122 move proximally as well. Each wedge 122 serially deforms and then separates staples 136 from the corresponding feeder belt 130, in substantially the same manner as set forth in the Endocutter Documents. During motion of each wedge 122, the feeder belt 130 may be held substantially in place, such as by tensioning between the wheels 132, 134. As each wedge 122 moves proximally, the proximal surface 123 of that wedge 122 contacts the distalmost staple 136 that is aligned with that wedge 122. The proximal surface 123 may be substantially vertical, or may be oriented in any other suitable direction. Contact between the proximal surface 123 and the staple 136 applies force to the staple 136, creating a moment about the connection between the staple 136 and the feeder belt 130. This moment rotates the staple 136 about the connection between the staple 136 and the feeder belt 130, such that the free end 138 of the staple 136 moves upward, out of the corresponding aperture 137 in the upper surface of the staple holder 12 and into the tissue held in the effector 16, then contacts the lower surface of the anvil 8. Optionally, a standard staple bending feature (not shown) may be defined in the surface of the anvil 8, at the location where the free end 138 of the staple 136 contacts the anvil 8. The rotation of the staple 136 about the connection between the staple 136 and the feeder belt 130 results in motion of the free end 138 both upward and distally. However, contact between the free end 138 of the staple 136 and the anvil 8 prevents further upward motion of the free end 138 of the staple 136. As a result, the free end 138 of the staple 136 bends, closing the staple 136. The staple 136 may be fabricated from a plastically-deformable material such as stainless steel, such that deformation of the staple 136 may be plastic deformation. Alternately, at least part of at least one staple 136 may be elastically deformable or superelastically deformable.

As each wedge 122 continues to move proximally, the upper surface of each wedge 122 approaches close to the corresponding staple 136, which may be already completely or substantially completely deformed against the anvil 8, and exerts a force on that staple 136 is primarily in the upward direction, at a location at or in proximity to the connection between the staple 136 and the feeder belt 130. That force shears, breaks or otherwise separates the closed staple 136 from the feeder belt 130. The connection between the staple 136 and the feeder belt 130 is configured such that the force exerted by the upper surface of the wedge 122 is sufficient to frangibly separate the staple 136 from the feeder belt 130 by shearing, breaking it off or otherwise separating it. The upper surface of the wedge 122 may also actively push, urge or otherwise eject the staple 136 completely out of the staple holder 12. Alternately, the staple 136 is passively ejected from the staple holder 12, meaning that the staple 136 is not affirmatively urged out of the staple holder 12; rather, it is simply allowed to exit therefrom. At this point, the deformed and ejected staple 136 is in position in the intestinal segment held in the effector 16. The frangibility of the staples 136 allows the staples 136 to be held securely and reliably by the feeder belt 130, and thus by the staple holder 12, while providing for reliable separation and deployment.

The wedge assembly 100 may continue its motion in the proximal direction, such that each wedge 122 continues to move proximally as well. Each wedge 122 then encounters another staple 136, and deforms that staple 136 and separates that staple 136 from the feeder belt 130 in substantially the same manner as described above. As the wedge assembly 100 moves proximally, the brick 106 slides along the inner side of the upper surface of the staple holder 12. The brick 106 is wider than the longitudinal slot 110 in the upper surface of the staple holder 12, and thus slides along the inner side of the upper surface of the staple holder 12 without snapping upward through that longitudinal slot 110. Engagement between the brick 106 and the inner side of the upper surface of the staple holder 12 lateral to the longitudinal slot 110 holds the linear cutter 2 clamped shut, such that it cannot be opened while the brick 106 is not in the brick engagement slot 108. In this way, the linear cutter 2 is affirmatively clamped shut in use to prevent incomplete deployment of staples 136. In order to bail out of a procedure in the middle, however, a user need only slide the deployment handle 50 to the initial position, returning the brick 106 to the brick engagement slot 108, then move the anvil assembly 4 upward to move the primer 60 out of engagement with the brick 106.

The wedge assembly 100 moves proximally until the engagement feature 102 encounters the proximal end 89 of the travel slot 88 in the adjustable tissue stop 70. As the linear cutter 2 moves to the closed configuration, the engagement feature 102 may move completely through the aperture 58 in the deployment handle 50, and upward out of that aperture 58 in the deployment handle 50 into the travel slot 88 in the adjustable tissue stop 70. Thus, as the wedge assembly 100 moves proximally, the engagement feature 102 moves proximally along the travel slot 88. The engagement feature 102 continues to slide proximally along the travel slot 88 until the engagement feature 102 reaches the proximal end 89 of the travel slot 88. Contact between the engagement feature 102 and the proximal end 89 of the travel slot 88 prevents further motion of the engagement feature 102, and thereby the wedge assembly 100, in the proximal direction. Due to engagement between at least one latch 78 of the adjustable tissue stop 70 and a corresponding latching slot 80, the contact between the engagement feature 102 and the proximal end 89 of the travel stop 88 does not move the adjustable tissue stop 70 proximally; that adjustable tissue stop 70 is substantially fixed in place. In this way, the proximal end 89 of the travel stop 88 defines the end of travel of the deployment handle 50 and thereby of the wedge assembly 100, defining the end of a staple line in tissue held in the effector 16. Thus, the adjustable tissue stop 70 controls the number of staples 136 deployed from the staple holder 12 during firing. Alternately, a feature on the deployment handle 50 itself extends upward into the travel slot 88, and the engagement feature 102 does not do so. The wedges 122 are staggered, as set forth above. The latching slots 80 on the anvil 8 may be located such that the proximal end 89 of the tissue stop 88 is located at a position that allows all of the wedges 122 to completely deform and separate a final staple 136 before beginning to engage a subsequent staple, when the engagement feature 102 contacts the proximal end 89 of the travel slot 88 and stops motion of the wedge assembly 100. The wedges 122 may be staggered in substantially the same manner as the staples 136 connected to the corresponding feeder belt 130, such that when travel of the wedges 122 is stopped, all of the staples 136 distal to the final, most-proximal location of the wedges 122 have been deformed and separated from the feeder belt 130. In this way, all of the staples 136 can be substantially longitudinally spaced substantially the same distance from one another along the corresponding feeder belt 130, without the need for blanks between groups of staples 136, or indeed without the need for grouping staples 136 at all. Consequently, a different length of staple line can be created during each use of the linear cutter 2.

Referring also to FIGS. 22-24, as the wedge assembly 100 moves proximally, the knife assembly 170 that is connected to the wedge assembly 100 moves proximally as well. In the initial position of the knife 178, at least the sharp proximal edge 180, and advantageously the entire knife 178, is located completely within the staple holder 12 such as in the knife pocket 199 such that it does not prematurely engage tissue, or pose a hazard to the user. As the wedge assembly 100 starts to move proximally from its initial position, the knife 178 is pulled proximally from its initial position as well. This proximal motion causes the guide pin 188 that extends laterally from the knife 178 to be pulled up the guide slot 194 in the knife insert 190. As the guide pin 188 rides up the guide slot 194, it moves the knife 178 upward and proximally as well. The sharp point 184 of the knife 178 is the first part of the knife 178 to move up and out of the knife insert 190 and then the knife slot 193 defined in the upper surface of the staple holder 12, such that the sharp point 184 encounters and incises tissue held in the effector 16. After the guide pin 188 reaches the top of the guide slot 194, it continues to move proximally along the knife travel platform 196 as the wedge assembly 100 continues to pull the knife assembly 170 proximally. As the knife 178 moves proximally, the sharp proximal edge 180 of the knife 178 incises tissue held in the effector 16. The incision of tissue may occur at a particular longitudinal location along the effector 16 during or after one or more staples 136 at that longitudinal location have been deformed and/or separated from the corresponding feeder belts 130, or may occur before one or more staples 136 at that longitudinal location have been deformed and/or separated from the corresponding feeder belts 130.

After the staples 136 have been deformed and ejected, and the knife 178 has transected the tissue held between the anvil 8 and the staple holder 12, the linear cutter 2 is unclamped, releasing the tissue held in the effector 16. The linear cutter 2 may be unclamped in any suitable manner. As one example, the unclamping may occur in substantially the reverse order of events set forth above. The deployment handle 50 is slid distally back to its initial position. The blunt distal edge 182 of the knife 178 touches tissue held in the effector 16, such that further incising is substantially not performed; rather, the knife 178 may return distally back to a position completely inside the knife pocket 199 in substantially the reverse motion as the motion described above with regard to motion of the knife 178 proximally. Each guide pin 188 rides back down the corresponding guide slot 194, directing the knife 178 back into the knife pocket 199. As the deployment handle 50 moves distally, it also moves the engagement feature 102 of the wedge assembly 100, and thus the wedge assembly 100 itself, in the distal direction back to its initial position.

Distal motion of the deployment handle 50 may also reset the staple holder 12 for subsequent deployment of another set of staples 136. Referring also to FIGS. 16-19, as the distal motion of the deployment handle 50 drives the wedge assembly 100 distally, each latch bump 142 enters a corresponding aperture 140 in a corresponding feeder belt 130. Each latch bump 142 is biased upward such as by the attached latch cantilever 144, so that if each latch bump 142 is not already in place in a corresponding aperture 140 when the wedge assembly 100 begins moving distally, then each latch bump 142 snaps upward into an aperture 140 as the wedge assembly 100 moves distally. After each latch bump 142 moves into engagement with a corresponding aperture 140, further distal motion of the wedge assembly 100 causes the feeder belt 130 in which that aperture 140 is defined to advance. The latch bump 142 may engage the corresponding aperture 140 in any manner. As one example, the distal end of the latch bump 142 may be substantially vertical, as may be the distal end of the aperture 140. Consequently, the vertical distal end of the latch bump 142 engages the distal end of the aperture 140 and pushes that distal end of the aperture 140, rather than slipping out of the aperture 140. A proximal portion of the latch bump 142 may be angled downward toward the proximal direction, forming a ramp, or may be shaped in any other suitable manner. In this way, when the wedge assembly 100 was previously moved proximally to deploy staples 136, each latch bump 142 did not engage apertures 140 in the feeder belt 130, but rather slid out of each aperture 140 during its proximal motion due to the angled shape of the proximal portion of the latch bump 142. That is, the force needed to slide the proximal portion of the latch bump 142 out of the corresponding aperture 140 in the feeder belt 130 is less than the force needed to advance the feeder belt 130. The motion of the feeder belt 130 during distal advancement of the wedge assembly 100 may be referred to as "advancing" the feeder belt 130, regardless of the fact that some or all of the feeder belt 130 may be moved in a direction other than distally during that advancing.

As the feeder belt 130 advances, the feeder belt 130 as a whole moves about the distal wheel 132 and the proximal wheel 134. The wheels 132, 134 may rotate, or at least one may be fixed in place such that each feeder belt 130 slides about the distal wheel 132 and/or the proximal wheel 134. As each feeder belt 130 advances, staples 136 may move about the proximal wheel 134 and/or the distal wheel 132. As set forth above, the staples 136 may be canted before and/or during their movement about a wheel 132, 134, such as by the use of a straightener 162. However, the staples 136 need not be canted for movement about a wheel 132, 134 if that wheel 132, 134 is sufficiently large in diameter, as set forth above. As each feeder belt 130 advances, fresh, unfired staples 136 are moved into position within the staple holder 12 for another firing of the linear cutter. Each feeder belt 130 is thereby reset.

The effector 16 is then unclamped, releasing the tissue previously held between the anvil 8 and the staple holder 12. The effector 16 may be unclamped in any suitable manner. As one example, the slider 38 of the clamp latch 32 may be depressed in the distal direction. As the slider 38 moves distally, the living hinge 36 is compressed distally, such that the ledge 40 moves distally out of engagement with the upper surface 44 of the staple holder 12 to a position underneath the slot 42. The ledge 40 is then free to move upward out of the slot 42, unlatching the anvil assembly 4 from the staple holder assembly 6. The first handle grip 10 may then be moved away from the second handle grip 14, thereby disengaging each fork 26 from the corresponding clamp pin 30. The effector 16 is then open, and the tissue may be removed. Such tissue may have been transected, at least partially, by the knife 178. At least one row of closed staples 136 may be located in that tissue on either side of the transection.

Next, the linear cutter 2 may be clamped and then fired again, substantially as described above. Because each feeder belt 130 has been advanced, staples 136 are in place for deployment, such that a user can deploy staples 136 from the staple holder 12 a second time without having to reload the staple holder 12. Advantageously, sufficient staples 136 are attached to each feeder belt 130 to enable four or more firings from the same staple holder 12. However, any suitable number of staples 136 may be attached to each feeder belt. The linear cutter 2 may be fired two or more times without changing a cartridge or other disposable staple holder, or reloading the staple holder 12 from outside the linear cutter 2.

After any deployment, the staple holder assembly 6 may be detached from the anvil assembly 4, such as by reversing the actions taken to attach the staple holder assembly 6 to the anvil assembly 4. If desired, a different staple holder assembly 6 may then be attached to the anvil assembly 4, such as when a staple holder assembly 6 is spent and additional staples 136 are required in the course of a surgical procedure. The different staple holder assembly 6 may hold staples 136 of a different size than the previously-utilized staple holder assembly 6. Because the staple holder assembly 6 can be exchanged after any deployment of staples 136, the linear cutter 2 provides flexibility in terms of usage, in that at any time the appropriate size staples 136 can be utilized simply by exchanging the staple holder assembly 6. Further, a staple holder assembly 6 may be fired at least once, removed from the anvil assembly 4, then reattached to the anvil assembly 4 at a later time, such as after at least one other staple holder assembly 6 has been attached to the anvil assembly 4, fired, and then been removed from the anvil assembly 4. After reattachment, deployment of staples 136 from that staple holder assembly 6 may continue to be performed as set forth above. In this way, a single anvil assembly 4 can be utilized to fire two or more different sizes of staples 136, simply by exchanging staple holder assemblies 6. Because each feeder belt 130 is advantageously reset before unclamping the linear cutter 2, as set forth above, staples 136 are in position for deployment when a previously-used staple holder assembly 6 is reconnected to the anvil assembly 4.

While the invention has been described in detail, it will be apparent to one skilled in the art that various changes and modifications can be made and equivalents employed, without departing from the present invention. It is to be understood that the invention is not limited to the details of construction, the arrangements of components, and/or the method set forth in the above description or illustrated in the drawings. Statements in the abstract of this document, and any summary statements in this document, are merely exemplary; they are not, and cannot be interpreted as, limiting the scope of the claims. Further, the figures are merely exemplary and not limiting. Words such as "upper," "lower," "upward," "downward" and the like are intended for the convenience of the reader and refer to the orientation and motion of parts on the printed page; they do not limit the orientation of the linear cutter 2 in use. Topical headings and subheadings are for the convenience of the reader only. They should not and cannot be construed to have any substantive significance, meaning or interpretation, and should not and cannot be deemed to indicate that all of the information relating to any particular topic is to be found under or limited to any particular heading or subheading. Therefore, the invention is not to be restricted or limited except in accordance with the following claims and their legal equivalents.

What is claimed is:

1. A surgical apparatus, comprising:
   an anvil assembly;
   a staple holder assembly detachably coupled to said anvil assembly;
   a feeder belt deposed at least partially within said staple holder assembly, wherein a plurality of staples are frangibly connected to said feeder belt;
   a wedge assembly slidably deposed within said staple holder assembly, wherein sliding said wedge assembly within said staple holder assembly in a first direction deploys and frangibly separates at least one of said plurality of staples connected to said feeder belt; and
   an adjustable tissue stop slidably coupled to said staple holder assembly or said anvil assembly, wherein the adjustable tissue stop defines an adjustable length of a staple line for deploying said plurality of staples.

2. The surgical apparatus of claim 1, further comprising:
   a knife assembly coupled to said wedge assembly wherein sliding said wedge assembly in said first direction activates a knife in said knife assembly, the activated knife slides along with said wedge assembly and transects a length of target tissue corresponding to the adjustable length of said staple line.

3. The surgical apparatus of claim 1, wherein the adjustable tissue stop defines an end of travel of said wedge assembly in said first direction.

4. The surgical apparatus of claim 1, wherein sliding said wedge assembly within said staple holder assembly in a second direction resets said wedge assembly to an initial position to further deploy additional staples.

5. The surgical apparatus of claim 1, wherein sliding said wedge assembly within said staple holder assembly in a second direction advances said feeder belt to place at least a fresh one of said plurality of staples in a ready fire or ready deployment position.

6. The surgical apparatus of claim 1, wherein advancing said feeder belt comprises of canting at least one of said plurality of staples.

7. The surgical apparatus of claim 1, wherein sliding said wedge in a second direction returns the knife back into said knife assembly and returns said knife assembly back to an initial position.

8. A surgical method for treating tissue, comprising:
placing an anvil assembly or a staple holder assembly near a target tissue;
coupling said anvil assembly with said staple holder assembly, wherein the staple holder assembly includes a feeder belt at least partially deposed within said staple holder assembly, and wherein a plurality of staples are frangibly connected to said feeder belt;
defining an adjustable length of a staple line for treating said target tissue;
sliding a wedge assembly within said staple holder in a first direction to deploy and frangibly separate at least one of said plurality of staples connected to said feeder belt; and
transecting a length of said target tissue corresponding to said defined adjustable length of said staple line.

9. The method of claim 8, wherein a distance for sliding said wedge assembly in said first direction corresponds to said defined adjustable length of said staple line.

10. The method of claim 8, wherein transecting said length of said target tissue comprises of activating a knife in a knife assembly and sliding said knife assembly along with said wedge assembly in said first direction.

11. The method of claim 8, further comprising;
sliding said wedge assembly within said staple holder in a second direction resets said wedge to an initial position to further deploy additional staples.

12. The method of claim 8, further comprising;
sliding said wedge assembly within said staple holder in a second direction advances said feeder belt placing at least a fresh one of said plurality of staples in a ready fire or ready deployment position.

13. The method of claim 8, further comprising:
sliding said wedge assembly within said staple holder in a second direction retracts said knife back into said knife assemble and returns said knife assembly to an initial position.

14. A surgical apparatus, comprising:
an anvil;
a staple holder coupled to and detachable in its entirety from said anvil;
a feeder belt deposed at least partially within said staple holder;
a plurality of staples separably attached to said feeder belt; and
an adjustable tissue stop movably coupled to at least one of said anvil and said staple holder, wherein said adjustable tissue stop limits movement of a wedge assembly along the anvil or staple holder to control a number of said plurality of staples for deployment from said staple holder.

15. A surgical apparatus, comprising:
an anvil assembly;
a staple holder assembly detachably coupled to said anvil assembly;
a feeder belt deposed at least partially within said staple holder assembly, wherein a plurality of staples are frangibly connected to said feeder belt;
a wedge assembly slidably deposed within said staple holder assembly, wherein sliding said wedge assembly within said staple holder assembly in a first direction deploys and frangibly separates at least one of said plurality of staples connected to said feeder belt and wherein sliding said wedge assembly within said staple holder assembly in a second direction resets said wedge assembly to an initial position to further deploy additional staples.

16. A surgical apparatus, comprising:
an anvil assembly;
a staple holder assembly detachably coupled to said anvil assembly;
a feeder belt deposed at least partially within said staple holder assembly, wherein a plurality of staples are frangibly connected to said feeder belt;
a wedge assembly slidably deposed within said staple holder assembly, wherein sliding said wedge assembly within said staple holder assembly in a first direction deploys and frangibly separates at least one of said plurality of staples connected to said feeder belt and wherein sliding said wedge assembly within said staple holder assembly in a second direction advances said feeder belt to place at least a fresh one of said plurality of staples in a ready fire or ready deployment position.

* * * * *